US012564655B1

(12) United States Patent (10) Patent No.: US 12,564,655 B1

Darr et al. (45) Date of Patent: Mar. 3, 2026

(54) SETTABLE SURGICAL COMPOSITIONS AND METHODS OF USE

(71) Applicant: Abyrx, Inc., Stamford, CT (US)

(72) Inventors: Aniq Darr, Riverdale, NY (US); John Pacifico, Greenwich, CT (US); Richard L. Kronenthal, Fair Lawn, NJ (US); Rao Bezwada, Stamford, CT (US); Bryant Heimbach, Stamford, CT (US)

(73) Assignee: Abyrx, Inc., Stamford, CT (US)

( * ) Notice: Subject to any disclaimer, the term of this patent is extended or adjusted under 35 U.S.C. 154(b) by 0 days.

(21) Appl. No.: 18/978,649

(22) Filed: Dec. 12, 2024

Related U.S. Application Data

(60) Provisional application No. 63/609,096, filed on Dec. 12, 2023.

(51) Int. Cl.
| | |
|---|---|
| *A61L 24/00* | (2006.01) |
| *A61L 24/02* | (2006.01) |
| *A61L 24/04* | (2006.01) |

(52) U.S. Cl.
CPC ........... *A61L 24/0015* (2013.01); *A61L 24/02* (2013.01); *A61L 24/046* (2013.01); *A61L 2300/112* (2013.01); *A61L 2300/406* (2013.01); *A61L 2430/02* (2013.01)

(58) Field of Classification Search
CPC .... A61L 24/0015; A61L 24/02; A61L 24/046; A61L 2300/112; A61L 2300/406; A61L 2430/02
See application file for complete search history.

(56) References Cited

U.S. PATENT DOCUMENTS

| | | | |
|---|---|---|---|
| 7,955,616 | B2 | 6/2011 | Kronenthal |
| 7,964,207 | B2 | 6/2011 | Deslauriers et al. |
| 7,985,414 | B2 | 7/2011 | Knaack et al. |
| 7,989,000 | B2 | 8/2011 | Kronenthal |
| 8,105,628 | B2 | 1/2012 | Kronenthal |
| 8,211,458 | B2 | 7/2012 | Deslauriers et al. |
| 8,309,131 | B2 | 11/2012 | Kronenthal |
| 8,337,497 | B2 | 12/2012 | Deslauriers et al. |
| 8,337,879 | B2 | 12/2012 | Kronenthal |
| 8,338,498 | B2 | 12/2012 | Deslauriers et al. |
| 8,603,528 | B2 | 12/2013 | Kronenthal |
| 8,668,697 | B2 | 3/2014 | Deslauriers et al. |
| 8,852,199 | B2 | 10/2014 | Deslauriers et al. |

(Continued)

FOREIGN PATENT DOCUMENTS

| | | |
|---|---|---|
| EP | 1613679 A1 | 1/2006 |
| EP | 1789088 A2 | 5/2007 |

(Continued)

OTHER PUBLICATIONS

Gessler, D.J et a., "GammaTile ®: Surgically targeted radiation therapy for glioblastomas," Future Oncol., 2020, 16(30):2445-2455. doi: 10.2217/fon-2020-0558.

(Continued)

*Primary Examiner* — Sameh R Boles

(74) *Attorney, Agent, or Firm* — Fenwick & West LLP

(57) ABSTRACT

Provided herein are settable bone hemostatic and adhesive compositions for use in surgical procedures comprising a variety of disclosed particles. Also provided are related compositions, including surgical kits and packages, as well as methods of making and using the compositions.

16 Claims, 1 Drawing Sheet

Antibiotic Concentration vs. Incubation Time

(56) References Cited

U.S. PATENT DOCUMENTS

| | | |
|---|---|---|
| 9,314,547 B2 | 4/2016 | Bezwada et al. |
| 9,827,349 B1 | 11/2017 | Pacifico et al. |
| 9,877,761 B2 | 1/2018 | Kapec et al. |
| 9,931,468 B1 | 4/2018 | Pacifico |
| 10,046,083 B2 | 8/2018 | Bezwada et al. |
| 10,201,338 B1 | 2/2019 | Pacifico et al. |
| 10,517,985 B2 | 12/2019 | Knaack et al. |
| 10,517,998 B2 | 12/2019 | Pacifico et al. |
| 10,525,160 B2 | 1/2020 | Bezwada et al. |
| 10,549,009 B2 | 2/2020 | Knaack et al. |
| 10,751,036 B1 | 8/2020 | Pacifico et al. |
| 11,116,866 B2 | 9/2021 | Bezwada et al. |
| 11,160,899 B2 | 11/2021 | Kronenthal et al. |
| 11,426,493 B2 | 8/2022 | Pacifico et al. |
| 11,642,435 B2 | 5/2023 | Knaack et al. |
| 11,672,885 B2 | 6/2023 | Kronenthal et al. |
| 12,048,775 B2 | 7/2024 | Kronenthal et al. |
| 2004/0127563 A1 | 7/2004 | Deslauriers |
| 2005/0031578 A1 | 2/2005 | Deslauriers et al. |
| 2010/0004745 A1 | 1/2010 | Deslauriers et al. |
| 2011/0201704 A1 | 8/2011 | Deslauriers et al. |
| 2012/0027817 A1 | 2/2012 | Kronenthal |
| 2012/0035610 A1 | 2/2012 | Deslauriers et al. |
| 2012/0189671 A1 | 7/2012 | Kronenthal |
| 2013/0109651 A1 | 5/2013 | Kronenthal |
| 2014/0066523 A1 | 3/2014 | Knaack et al. |
| 2014/0275287 A1 | 9/2014 | Knaack et al. |
| 2019/0134259 A1* | 5/2019 | Kronenthal ............. A61L 24/02 |
| 2020/0046874 A1 | 2/2020 | Kronenthal et al. |
| 2022/0241457 A1 | 8/2022 | Pacifico et al. |
| 2023/0191004 A1 | 6/2023 | Pacifico et al. |
| 2023/0330301 A1 | 10/2023 | Kronenthal |
| 2024/0335584 A1 | 10/2024 | Darr et al. |
| 2025/0065019 A1 | 2/2025 | Pacifico et al. |
| 2025/0073375 A1 | 3/2025 | Kronenthal et al. |

FOREIGN PATENT DOCUMENTS

| | | |
|---|---|---|
| EP | 1912630 A2 | 4/2008 |
| EP | 2306936 A2 | 4/2011 |
| EP | 2462958 A2 | 6/2012 |
| EP | 2608721 A2 | 7/2013 |
| EP | 1677664 B1 | 7/2014 |
| EP | 2773358 A1 | 9/2014 |
| EP | 2801376 A1 | 11/2014 |
| EP | 2462957 B1 | 4/2019 |
| EP | 3528857 A1 | 8/2019 |
| EP | 3630210 A1 | 4/2020 |
| EP | 3706815 A1 | 9/2020 |
| EP | 2753371 B1 | 8/2021 |
| EP | 3925637 A1 | 12/2021 |
| EP | 4284454 A1 | 12/2023 |
| EP | 4380640 A1 | 6/2024 |
| EP | 4511077 A1 | 2/2025 |
| EP | 3821916 B1 | 3/2025 |
| WO | WO-2005034726 A2 | 4/2005 |
| WO | WO-2005094553 A2 | 10/2005 |
| WO | WO-2007014210 A2 | 2/2007 |
| WO | WO-2010002551 A2 | 1/2010 |
| WO | WO-2011044209 A2 | 4/2011 |
| WO | WO-2011103268 A2 | 8/2011 |
| WO | WO-2012027025 A2 | 3/2012 |
| WO | WO-2012151196 A1 | 11/2012 |
| WO | WO-2012170700 A2 | 12/2012 |
| WO | WO-2013036525 A2 | 3/2013 |
| WO | WO-2013067154 A1 | 5/2013 |
| WO | WO-2018075866 A1 | 4/2018 |
| WO | WO-2018222743 A1 | 12/2018 |
| WO | WO-2019094463 A1 | 5/2019 |
| WO | WO-2022165319 A1 | 8/2022 |
| WO | WO-2023014592 A1 | 2/2023 |
| WO | WO-2023205141 A1 | 10/2023 |
| WO | WO-2024064891 A1 | 3/2024 |

OTHER PUBLICATIONS

Stravinskas et al., "Pharmacokinetics of gentamicin eluted from a regenerating bone graft substitute: In vitro and clinical release studies," Bone Joint Res., Sep. 2016, 5(9):427-35. doi. 10.1302/2046-758.59.BJR-2016-0108.R1.v.

* cited by examiner

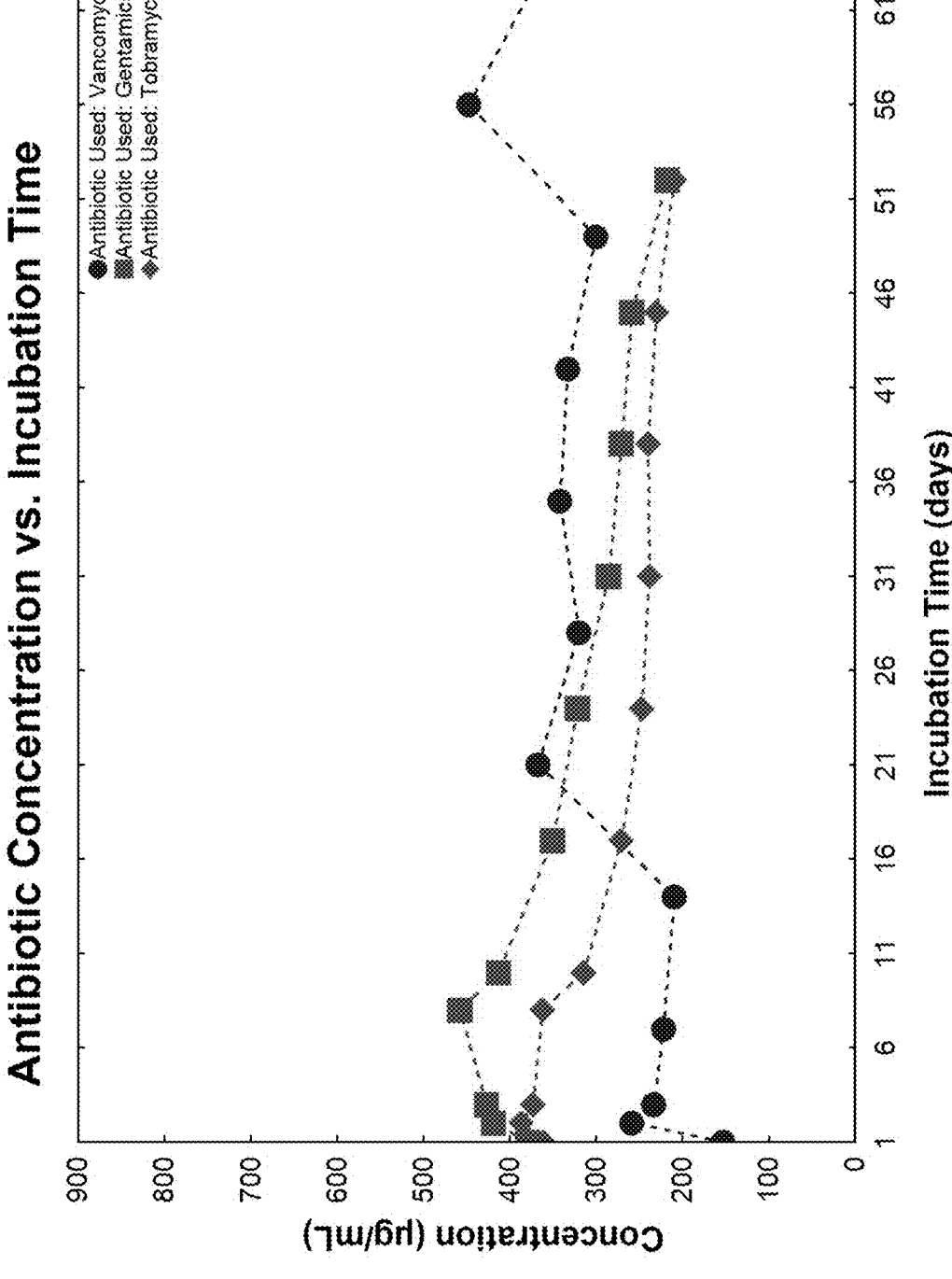

SETTABLE SURGICAL COMPOSITIONS AND METHODS OF USE

RELATED APPLICATIONS

This application claims priority to U.S. Provisional Application No. 63/609,096, filed Dec. 12, 2023, the contents of which are herein incorporated by reference in their entirety.

BACKGROUND

Bone cements, pastes, and putties are used during surgery to aid in bone hemostasis, bone repair and bone reconstruction. However, existing cements, pastes, and putties, including those that are calcium phosphate/sulfate and magnesium-based, exhibit undesirable properties such as brittleness, which limits their clinical effectiveness. Accordingly, there is a need in the art for improved compositions for use as bone cements, pastes, and putties.

SUMMARY

The present disclosure provides reactive compositions which can be mixed together to produce a composition which cures into a final, hardened form. Without wishing to be bound by theory, these reactive compositions comprise amounts of reagents which react and cure into a final, hardened form. Prior to curing into the final, hardened form, the compositions which are formed by mixing together two or more reactive compositions described herein are settable and moldable, allowing them to be used in various surgical applications, including, but not limited to, bone hemostasis, bone repair and bone reconstruction. Accordingly, the present disclosure also provides compositions which are the result of mixing of the reactive compositions described herein. The compositions that are formed by the mixing of two or more of the reactive compositions described herein can be absorbable or nonabsorbable.

Any of the above aspects and any aspect described herein can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The above and further features will be more clearly appreciated from the following detailed description when taken in conjunction with the accompanying drawings.

FIG. 1 shows the results from experiments described in Example 1 of the present disclosure that analyze the concentration of antibiotics in final product compositions of the present disclosure over time.

DETAILED DESCRIPTION

Compositions of the Present Disclosure

The present disclosure provides reactive compositions which can be mixed together to produce a composition which cures into a final, hardened form. Without wishing to be bound by theory, these reactive compositions comprise amounts of reagents which react and cure into a final, hardened form. Prior to curing into the final, hardened form, the compositions which are formed by mixing together two or more reactive compositions described herein are settable and moldable, allowing them to be used in various surgical applications, including, but not limited to, bone hemostasis, bone repair and bone reconstruction. Accordingly, the present disclosure also provides compositions which are the result of mixing of the reactive compositions described herein. The compositions that are formed by the mixing of two or more of the reactive compositions described herein can be absorbable or nonabsorbable.

In some aspects, any of the compositions of the present disclosure can comprise [5-[2-[2-(4-Isocyanatobenzoyl) oxypropanoyloxy]-ethoxy]-1-methyl-2-oxo-pentyl]-4-iso-cyanatobenzoate, which is referred to herein as "Absorbable Lactide Diester" or "ALD".

In some aspects, any of the compositions of the present disclosure can comprise 1,1,1-tris-(4-isocyanatophenoxym-ethyl)-propane, which is referred to herein as "TMPI".

In some aspects, any of the compositions of the present disclosure can comprise polycaprolactone triol, which is referred to herein as "PCL".

In some aspects, any of the compositions of the present disclosure can comprise 1,4 butane diol, which is referred to herein as "BDO".

In some aspects, any of the compositions of the present disclosure can comprise triethanolamine, referred to herein as "TEA".

In some aspects, any of the compositions of the present disclosure can comprise trimethylolpropane ethoxylate with an average Mn of 170, which is referred to herein as "TMPE170".

In some aspects, any of the compositions of the present disclosure can comprise trimethylolpropane ethoxylate with an average Mn of 450, which is referred to herein as "TMPE450".

In some aspects, any of the compositions of the present disclosure can comprise trimethylolpropane ethoxylate compound (i.e., "TPME"). As a non-limiting example, the compositions of the present disclosure can comprise trimethyl-olpropane ethoxylate compound with an average Mn between 170-450. In some aspects, the compositions of the present disclosure can comprise trimethylolpropane ethoxylate compound with an average Mn less than 170 or with an average Mn greater than 450.

In some aspects, any of the compositions of the present disclosure can comprise N,N,N',N'-Tetrakis(2-Hydroxypropyl)ethylenediamine, referred to herein as "TKP".

In some aspects, any of the compositions of the present disclosure can comprise tocopherol acetate, referred to herein as "TA".

In some aspects, any of the compositions of the present disclosure can comprise triacetin.

In some aspects, any of the compositions of the present disclosure can comprise paraffin oil.

In some aspects, any of the compositions of the present disclosure can comprise calcium stearate.

In some aspects, any of the compositions of the present disclosure can comprise biphasic hydroxyapatite and β-tricalcium phosphate granules, referred to herein as "HA/β-TCP granules".

In some aspects, any of the compositions of the present disclosure can comprise β-tricalcium phosphate powder, referred to herein as "β-TCP powder" or "milled β-TCP".

In some aspects, any of the compositions of the present disclosure can comprise hydroxyapatite powder, referred to herein as "HA powder" or "milled HA".

In some aspects, any of the compositions of the present disclosure can comprise calcium phosphate or a calcium phosphate derivative (e.g., calcium phosphate, HA/β-TCP, β-TCP, hydroxyapatite).

In some aspects, any of the compositions of the present disclosure can comprise barium sulfate ($BaSO_4$).

In some aspects, any of the compositions of the present disclosure can be stable at room temperature (i.e., shelf stability) for at least 6 months. In some aspects, any of the compositions of the present disclosure can be stable at room temperature (i.e., shelf stability) for more than 6 months. In some aspects, any of the compositions of the present disclosure can be stable at room temperature (i.e., shelf stability) for at least 1 year, or 2 years, or 3 years. In some aspects, any of the compositions of the present disclosure can be stable at room temperature (i.e., shelf stability) for more than 3 years.

In some aspects, any of the compositions of the present disclosure can be mixed to form a homogenous mixture (i.e., mixability to homogeneity) within 1 minute. In some aspects, any of the compositions of the present disclosure can be mixed by hand.

In some aspects, any of the compositions of the present disclosure can be extruded during manufacturing using pressures of less than 35 pounds per square inch (psi).

In some aspects, any of the compositions of the present disclosure can be mixed to form a dark color or a light color, wherein the final color can be contrasted against additional or alternate constituents that may be added.

In some aspects, any of the compositions of the present disclosure have a suitable viscosity for filling a syringe. In some aspects, any of the compositions of the present disclosure have a suitable viscosity for easily dispensing through a cannula with an inner diameter of as low as 2 millimeters (mm). In some aspects, any of the compositions of the present disclosure have a suitable viscosity for easily mixing using standard equipment and/or static mixing equipment. In some aspects, any of the compositions of the present disclosure can be mixed, prepared, or combined and further easily spread (i.e., spreadability) at the application site over at least 30 seconds. In some aspects, any of the compositions of the present disclosure can be mixed, prepared, or combined and further easily spread at the application site over at least 1 minute, or at least 2 minutes, or at least 3 minutes, or at least 4 minutes, or at least 5 minutes.

In some aspects, any of the compositions of the present disclosure can be mixed, prepared, or combined and further easily spread over a surface, wherein about 0.25 cubic centimeters (cc) of the composition is applied as a thin layer over a surface greater than about 2 centimeters (cm). In some aspects, any of the compositions of the present disclosure demonstrate immediate physical properties that allow for securing and/or holding bone fragments together and allow for fragment manipulation for at least 30 seconds. In some aspects, any of the compositions of the present disclosure demonstrate immediate physical properties that allow for securing and/or holding bone fragments together and allow for fragment manipulation, for example, by the surgeon, for at least 1 minute or at least 2 minutes.

In some aspects, any of the compositions of the present disclosure allow for hardware insertion (e.g., a surgical screw) after application of the composition without the use of a drill or related tools. In some aspects, any of the compositions of the present disclosure allow for hardware insertion (e.g., a surgical screw) after at least 30 seconds post-application of the composition to the subject without the use of a drill or related tools. In some aspects, any of the compositions of the present disclosure allow for hardware insertion (e.g., a surgical screw) after at least 1 minute, or at least 2 minutes, or at least 3 minutes, or at least 4 minutes post-application of the composition to the subject without the use of a drill or related tools.

In some aspects, any of the compositions of the present disclosure can be manipulated with powered orthopedic tools (e.g., a burr, a drill, a saw, a reamer, etc.) over the course of at least 30 seconds, or at least 1 minute, or at least 2 minutes, or at least 3 minutes post-application of the composition to the subject.

In some aspects, any of the compositions of the present disclosure resist irrigation at the site of application to the subject. In some aspects, some of the compositions of the present disclosure resist bodily absorption or dispersion.

In some aspects, any of the compositions of the present disclosure demonstrate a volumetric expansion of no more than about 10%. In some aspects, any of the compositions of the present disclosure demonstrate a volumetric expansion of no more than about 12%.

The present disclosure provides reactive compositions, which are the result of the mixing and/or reacting constituent components of any one of the Reactive Compositions A, B, C, D, E, F, G, H, I, J, K, L, M, N, O, or any combination thereof. The present disclosure provides for a composition that is the product of mixing two or more constituents, such as mixing a compound comprising isocyanate groups (e.g., ALD or TPMI) with at least one polyol. In some aspects, the mixing of the constituents within Reactive Compositions A-O forms a pre-polymer. As a non-limiting example, for Reactive Composition A provided below, the present disclosure provides for a composition that is the product of mixing about 34.1 wt % ALD, about 2.7 wt % PCL, about 6.5 wt % tocopherol acetate, about 51.7 wt % HA/β-TCP granules, and about 4.9 wt % β-TCP powder.

Reactive Composition A

The present disclosure provides a reactive composition referred to herein as reactive "Reactive Composition A."

In some aspects, Reactive Composition A comprises about 33.1 wt % to about 35.1 wt % ALD. In some aspects, Reactive Composition A comprises about 34.1 wt % ALD.

In some aspects, Reactive Composition A comprises about 1.7 wt % to about 3.7 wt % PCL. In some aspects, Reactive Composition A comprises about 2.7 wt % PCL.

In some aspects, Reactive Composition A comprises about 5.5 wt % to about 7.5 wt % tocopherol acetate. in some aspects, Reactive Composition A comprises about 6.5 wt % tocopherol acetate.

In some aspects, Reactive Composition A comprises about 50.7 wt % to about 52.7 wt % HA/β-TCP granules. In some aspects, Reactive Composition A comprises about 51.7 wt % HA/β-TCP granules.

In some aspects, Reactive Composition A comprises about 3.9 wt % to about 5.9 wt % β-TCP powder. In some aspects, Reactive Composition A comprises about 4.9 wt % β-TCP powder.

In some aspects, Reactive Composition A comprises about 56.6 wt % of calcium phosphate or a calcium phosphate-based compound (e.g., calcium phosphate, a calcium phosphate derivate, β-TCP, HA/β-TCP, or a combination thereof).

Accordingly, in some aspects, Reactive Composition A comprises, consists of, or consists essentially of about 33.1 wt % to about 35.1. wt % ALD, about 1.7 wt % to about 3.7 wt % PCL, about 5.5 wt % to about 7.5 wt % tocopherol acetate, about 50.7 wt % to about 52.7 wt % HA/β-TCP granules, and about 3.9 wt % to about 5.9 wt % β-TCP powder.

Accordingly, in some aspects, Reactive Composition A comprises, consists of, or consists essentially of about 34.1 wt % ALD, about 2.7 wt % PCL, about 6.5 wt % tocopherol acetate, about 51.7 wt % HA/β-TCP granules, and about 4.9 wt % β-TCP powder.

In some aspects, Reactive Composition A is a putty.

In some aspects, Reactive Composition A comprises a pre-polymer formed from the reaction between isocyanate groups and polyol groups. In some aspects, Reactive Composition A comprises a percentage of reacted and unreacted isocyanate and/or reacted and unreacted polyol. In some aspects, Reactive Composition A comprises about 7.3 wt % of reacted isocyanate. In some aspects, Reactive Composition A comprises about 26.8 wt % of unreacted isocyanate.

As would be understood in the art, the reacted percent can also be expressed as a percentage of the total isocyanate (i.e., —NCO) or hydroxyl (i.e., —OH) functional groups. In some aspects, Reactive Composition A comprises about 21.5% reacted isocyanate groups. In some aspects, Reactive Composition A comprises about 78.5% unreacted isocyanate groups.

Reactive Composition B

The present disclosure provides a reactive composition referred to herein as reactive "Reactive Composition B."

In some aspects, Reactive Composition B comprises about 5.9 wt % to about 7.9 wt % ALD. In some aspects, Reactive Composition B comprises about 6.9 wt % ALD.

In some aspects, Reactive Composition B comprises about 4.3 wt % to about 6.3 wt % PCL. In some aspects, Reactive Composition B comprises about 5.3 wt % PCL.

In some aspects, Reactive Composition B comprises about 0.9 wt % to about 2.9 wt % BDO. In some aspects, Reactive Composition B comprises about 1.9 wt % BDO.

In some aspects, Reactive Composition B comprises about 2.8 wt % to about 4.8 wt % tocopherol acetate. in some aspects, Reactive Composition B comprises about 3.8 wt % tocopherol acetate.

In some aspects, Reactive Composition B comprises about 1.3 wt % to about 3.3 wt % triacetin. In some aspects, Reactive Composition B comprises about 2.3 wt % triacetin.

In some aspects, Reactive Composition B comprises about 0.1 wt % to about 1.6 wt % calcium stearate. In some aspects, Reactive Composition B comprises about 0.6 wt % calcium stearate.

In some aspects, Reactive Composition B comprises about 18.3 wt % to about 20.3 wt % HA/β-TCP granules. In some aspects, Reactive Composition B comprises about 19.3 wt % HA/β-TCP granules.

In some aspects, Reactive Composition B comprises about 59 wt % to about 61 wt % β-TCP powder. In some aspects, Reactive Composition B comprises about 60 wt % β-TCP powder.

In some aspects, Reactive Composition B comprises about 79.3 wt % of calcium phosphate or a calcium phosphate-based compound (e.g., calcium phosphate, a calcium phosphate derivate, β-TCP, HA/β-TCP, or a combination thereof).

Accordingly, in some aspects, Reactive Composition B comprises, consists of, or consists essentially of about 5.9 wt % to about 7.9 wt % ALD, about 4.3 wt % to about 6.3 wt % PCL, about 0.9 wt % to about 2.9 wt % BDO, about 2.8 wt % to about 4.8 wt % tocopherol acetate, about 1.3 wt % to about 3.3 wt % triacetin, about 0.1 wt % to about 1.6 wt % calcium stearate, about 18.3 wt % to about 20.3 wt % HA/β-TCP granules, about 59 wt % to about 61 wt % β-TCP powder.

Accordingly, in some aspects, Reactive Composition B comprises, consists of, or consists essentially of about 6.9 wt % ALD, about 5.3 wt % PCL, about 1.9 wt % BDO, about 3.8 wt % tocopherol acetate, about 2.3 wt % triacetin, about 0.6 wt % calcium stearate, about 19.3 wt % HA/β-TCP granules, and about 60 wt % β-TCP powder.

In some aspects, Reactive Composition B is a putty.

In some aspects, Reactive Composition B comprises a pre-polymer formed from the reaction between isocyanate groups and polyol groups. In some aspects, Reactive Composition B comprises a percentage of reacted and unreacted isocyanate and/or reacted and unreacted polyol. In some aspects, Reactive Composition B comprises about 2.5 wt % of reacted prepolymer polyol. In some aspects, Reactive Composition B comprises about 2.7 wt % of unreacted prepolymer polyol. In some aspects, Reactive Composition B comprises about 1.9 wt % of reacted total polyol. In some aspects, Reactive Composition B comprises about 5.3 wt % of unreacted total polyol.

As would be understood in the art, the reacted percent can also be expressed as a percentage of the total isocyanate (i.e., —NCO) or hydroxyl (i.e., —OH) functional groups. In some aspects, Reactive Composition B comprises about 26.8% reacted hydroxyl groups. In some aspects, Reactive Composition B comprises about 73.2% unreacted hydroxyl groups.

Reactive Composition C

The present disclosure provides a reactive composition referred to herein as reactive "Reactive Composition C."

In some aspects, Reactive Composition C comprises about 4.2 wt % to about 6.2 wt % ALD. In some aspects, Reactive Composition C comprises about 5.2 wt % ALD.

In some aspects, Reactive Composition C comprises about 3 wt % to about 5 wt % PCL. In some aspects, Reactive Composition C comprises about 4 wt % PCL.

In some aspects, Reactive Composition C comprises about 0.1 wt % to about 2.1 wt % BDO. In some aspects, Reactive Composition C comprises about 1.1 wt % BDO.

In some aspects, Reactive Composition C comprises about 1.6 wt % to about 3.6 wt % TEA. In some aspects, Reactive Composition C comprises about 2.6 wt % TEA.

In some aspects, Reactive Composition C comprises about 3.6 wt % to about 5.6 wt % tocopherol acetate. in some aspects, Reactive Composition C comprises about 4.6 wt % tocopherol acetate.

In some aspects, Reactive Composition C comprises about 1.2 wt % to about 3.2 wt % triacetin. In some aspects, Reactive Composition C comprises about 2.2 wt % triacetin.

In some aspects, Reactive Composition C comprises about 0.1 wt % to about 1.4 wt % calcium stearate. In some aspects, Reactive Composition C comprises about 0.4 wt % calcium stearate.

In some aspects, Reactive Composition C comprises about 14.2 wt % to about 16.2 wt % HA/β-TCP granules. In some aspects, Reactive Composition C comprises about 15.2 wt % HA/β-TCP granules.

In some aspects, Reactive Composition C comprises about 63.7 wt % to about 65.7 wt % β-TCP powder. In some aspects, Reactive Composition C comprises about 64.7 wt % β-TCP powder.

In some aspects, Reactive Composition C comprises about 79.9 wt % of calcium phosphate or a calcium phosphate-based compound (e.g., calcium phosphate, a calcium phosphate derivate, β-TCP, HA/β-TCP, or a combination thereof).

Accordingly, in some aspects, Reactive Composition C comprises, consists of, or consists essentially of about 4.2 wt % to about 6.2 wt % ALD, about 3 wt % to about 5 wt % PCL, about 0.1 wt % to about 2.1 wt % BDO, about 1.6 wt % to about 3.6 wt % TEA, about 3.6 wt % to about 5.6 wt % tocopherol acetate, about 1.2 wt % to about 3.2 wt % triacetin, about 0.1 wt % to about 1.4 wt % calcium stearate, about 14.2 wt % to about 16.2 wt % HA/β-TCP granules, and about 63.7 wt % to about 65.7 wt % β-TCP powder.

Accordingly, in some aspects, Reactive Composition C comprises, consists of, or consists essentially of about 5.2 wt % ALD, about 4 wt % PCL, about 1.1 wt % BDO, about 2.6 wt % TEA, about 4.6 wt % tocopherol acetate, about 2.2 wt % triacetin, about 0.4 wt % calcium stearate, about 15.2 wt % HA/β-TCP granules, and about 64.7 wt % β-TCP powder.

In some aspects, Reactive Composition C is a putty.

In some aspects, Reactive Composition C comprises a pre-polymer formed from the reaction between isocyanate groups and polyol groups. In some aspects, Reactive Composition C comprises a percentage of reacted and unreacted isocyanate and/or reacted and unreacted polyol. In some aspects, Reactive Composition C comprises about 1.9 wt % of reacted prepolymer polyol. In some aspects, Reactive Composition C comprises about 2.1 wt % of unreacted prepolymer polyol. In some aspects, Reactive Composition C comprises about 1.3 wt % of reacted total polyol. In some aspects, Reactive Composition C comprises about 6.4 wt % of unreacted total polyol.

As would be understood in the art, the reacted percent can also be expressed as a percentage of the total isocyanate (i.e., —NCO) or hydroxyl (i.e., —OH) functional groups. In some aspects, Reactive Composition C comprises about 16.4% reacted hydroxyl groups. In some aspects, Reactive Composition C comprises about 83.6% unreacted hydroxyl groups.

Reactive Composition D

The present disclosure provides a reactive composition referred to herein as reactive "Reactive Composition D."

In some aspects, Reactive Composition D comprises about 38.9 wt % to about 40.9 wt % ALD. In some aspects, Reactive Composition D comprises about 39.9 wt % ALD.

In some aspects, Reactive Composition D comprises about 6.2 wt % to about 8.2 wt % tocopherol acetate. In some aspects, Reactive Composition D comprises about 7.2 wt % tocopherol acetate.

In some aspects, Reactive Composition D comprises about 0.01 wt % to about 1.1 wt % calcium stearate. In some aspects, Reactive Composition D comprises about 0.1 wt % calcium stearate.

In some aspects, Reactive Composition D comprises about 6.9 wt % to about 8.9 wt % β-TCP powder. In some aspects, Reactive Composition D comprises about 7.9 wt % β-TCP powder.

In some aspects, Reactive Composition D comprises about 43.8 wt % to about 45.8 wt % HA powder. In some aspects, Reactive Composition D comprises about 44.8 wt % HA powder.

In some aspects, Reactive Composition D comprises about 52.7 wt % of calcium phosphate or a calcium phosphate-based compound (e.g., calcium phosphate, a calcium phosphate derivate, β-TCP, HA/β-TCP, or a combination thereof).

Accordingly, in some aspects, Reactive Composition D comprises, consists of, or consists essentially of about 38.9 wt % to about 40.9 wt % ALD, about 6.2 wt % to about 8.2 wt % tocopherol acetate, about 0.01 wt % to about 1.1 wt % calcium stearate, about 6.9 wt % to about 8.9 wt % β-TCP powder, and about 43.8 wt % to about 45.8 wt % HA powder.

Accordingly, in some aspects, Reactive Composition D comprises, consists of, or consists essentially of about 39.9 wt % ALD, about 7.2 wt % tocopherol acetate, about 0.1 wt % calcium stearate, about 7.9 wt % β-TCP powder, and about 44.8 wt % HA powder.

In some aspects, Reactive Composition D is a paste.

In some aspects, Reactive Composition D comprises a pre-polymer formed from the reaction between isocyanate groups and polyol groups. In some aspects, Reactive Composition D comprises a percentage of reacted and unreacted isocyanate and/or reacted and unreacted polyol. In some aspects, Reactive Composition D comprises about 0 wt % of reacted isocyanate. In some aspects, Reactive Composition D comprises about 39.9 wt % of unreacted isocyanate.

As would be understood in the art, the reacted percent can also be expressed as a percentage of the total isocyanate (i.e., —NCO) or hydroxyl (i.e., —OH) functional groups. In some aspects, Reactive Composition D comprises about 0% reacted isocyanate groups. In some aspects, Reactive Composition D comprises about 100% unreacted isocyanate groups.

Reactive Composition E

The present disclosure provides a reactive composition referred to herein as reactive "Reactive Composition E."

In some aspects, Reactive Composition E comprises about 0.1 wt % to about 1.9 wt % ALD. In some aspects, Reactive Composition E comprises about 0.9 wt % ALD.

In some aspects, Reactive Composition E comprises about 27.6 wt % to about 29.6 wt % PCL. In some aspects, Reactive Composition E comprises about 28.6 wt % PCL.

In some aspects, Reactive Composition E comprises about 0.1 wt % to about 1.9 wt % BDO. In some aspects, Reactive Composition E comprises about 0.9 wt % BDO.

In some aspects, Reactive Composition E comprises about 6.9 wt % to about 8.9 wt % TEA. In some aspects, Reactive Composition E comprises about 7.9 wt % TEA.

In some aspects, Reactive Composition E comprises about 0.1 wt % to about 1.2 wt % triacetin. In some aspects, Reactive Composition E comprises about 0.2 wt % triacetin.

In some aspects, Reactive Composition E comprises about 0.9 wt % to about 2.9 wt % calcium stearate. In some aspects, Reactive Composition E comprises about 1.9 wt % calcium stearate.

In some aspects, Reactive Composition E comprises about 58.6 wt % to about 60.6 wt % HA powder. In some aspects, Reactive Composition E comprises about 59.6 wt % HA powder.

In some aspects, Reactive Composition E comprises about 59.6 wt % of calcium phosphate or a calcium phosphate-based compound (e.g., calcium phosphate, a calcium phosphate derivate, β-TCP, HA/β-TCP, or a combination thereof).

Accordingly, in some aspects, Reactive Composition E comprises, consists of, or consists essentially of about 0.1 wt % to about 1.9 wt % ALD, about 27.6 wt % to about 29.6 wt % PCL, about 0.1 wt % to about 1.9 wt % BDO, about 6.9 wt % to about 8.9 wt % TEA, about 0.1 wt % to about 1.2 wt % triacetin, about 0.9 wt % to about 2.9 wt % calcium stearate, and about 58.6 wt % to about 60.6 wt % HA powder.

Accordingly, in some aspects, Reactive Composition E comprises, consists of, or consists essentially of about 0.9 wt % ALD, about 28.6 wt % PCL, about 0.9 wt % BDO, about 7.9 wt % TEA, about 0.2 wt % triacetin, about 1.9 wt % calcium stearate, and about 59.6 wt % HA powder.

In some aspects, Reactive Composition E is a paste.

In some aspects, Reactive Composition E comprises a pre-polymer formed from the reaction between isocyanate groups and polyol groups. In some aspects, Reactive Composition E comprises a percentage of reacted and unreacted isocyanate and/or reacted and unreacted polyol. In some aspects, Reactive Composition E comprises about 0.3 wt % of reacted prepolymer polyol. In some aspects, Reactive Composition E comprises about 28.2 wt % of unreacted prepolymer polyol. In some aspects, Reactive Composition E comprises about 0.3 wt % of reacted total polyol. In some aspects, Reactive Composition E comprises about 37.2 wt % of unreacted total polyol.

As would be understood in the art, the reacted percent can also be expressed as a percentage of the total isocyanate (i.e., —NCO) or hydroxyl (i.e., —OH) functional groups. In some aspects, Reactive Composition E comprises about 0.7% reacted hydroxyl groups. In some aspects, Reactive Composition E comprises about 99.3% unreacted hydroxyl groups.

Reactive Composition F

The present disclosure provides a reactive composition referred to herein as reactive "Reactive Composition F."

In some aspects, Reactive Composition F comprises about 29.2 wt % to about 31.2 wt % ALD. In some aspects, Reactive Composition F comprises about 30.2 wt % ALD.

In some aspects, Reactive Composition F comprises about 1.4 wt % to about 3.4 wt % PCL. In some aspects, Reactive Composition F comprises about 2.4 wt % PCL.

In some aspects, Reactive Composition F comprises about 5.8 wt % to about 7.8 wt % tocopherol acetate. in some aspects, Reactive Composition F comprises about 6.8 wt % tocopherol acetate.

In some aspects, Reactive Composition F comprises about 55.2 wt % to about 57.2 wt % HA/β-TCP granules. In some aspects, Reactive Composition F comprises about 56.2 wt % HA/β-TCP granules.

In some aspects, Reactive Composition F comprises about 3.4 wt % to about 5.4 wt % β-TCP powder. In some aspects, Reactive Composition F comprises about 4.4 wt % β-TCP powder.

In some aspects, Reactive Composition F comprises about 60.6 wt % of calcium phosphate or a calcium phosphate-based compound (e.g., calcium phosphate, a calcium phosphate derivate, β-TCP, HA/β-TCP, or a combination thereof).

Accordingly, in some aspects, Reactive Composition F comprises, consists of, or consists essentially of about 29.2 wt % to about 31.2 wt % ALD, about 1.4 wt % to about 3.4 wt % PCL, about 5.8 wt % to about 7.8 wt % tocopherol acetate, about 55.2 wt % to about 57.2 wt % HA/β-TCP granules, and about 3.4 wt % to about 5.4 wt % β-TCP powder.

Accordingly, in some aspects, Reactive Composition F comprises, consists of, or consists essentially of about 30.2 wt % ALD, about 2.4 wt % PCL, about 6.8 wt % tocopherol acetate, about 56.2 wt % HA/β-TCP granules, and about 4.4 wt % β-TCP powder.

In some aspects, Reactive Composition F is a putty.

In some aspects, Reactive Composition F comprises a pre-polymer formed from the reaction between isocyanate groups and polyol groups. In some aspects, Reactive Composition F comprises a percentage of reacted and unreacted isocyanate and/or reacted and unreacted polyol. In some aspects, Reactive Composition F comprises about 6.4 wt % of reacted isocyanate. In some aspects, Reactive Composition F comprises about 23.8 wt % of unreacted isocyanate.

As would be understood in the art, the reacted percent can also be expressed as a percentage of the total isocyanate (i.e., —NCO) or hydroxyl (i.e., —OH) functional groups. In some aspects, Reactive Composition F comprises about 21.2% reacted isocyanate groups. In some aspects, Reactive Composition F comprises about 78.8% unreacted isocyanate groups.

Reactive Composition G

The present disclosure provides a reactive composition referred to herein as reactive "Reactive Composition G."

In some aspects, Reactive Composition G comprises about 3.6 wt % to about 5.6 wt % ALD. In some aspects, Reactive Composition G comprises about 4.6 wt % ALD.

In some aspects, Reactive Composition G comprises about 6.6 wt % to about 8.6 wt % PCL. In some aspects, Reactive Composition G comprises about 7.6 wt % PCL.

In some aspects, Reactive Composition G comprises about 0.1 wt % to about 1.2 wt % BDO. In some aspects, Reactive Composition G comprises about 0.2 wt % BDO.

In some aspects, Reactive Composition G comprises about 2.5 wt % to about 4.5 wt % tocopherol acetate. in some aspects, Reactive Composition G comprises about 3.5 wt % tocopherol acetate.

In some aspects, Reactive Composition G comprises about 2.1 wt % to about 4.1 wt % triacetin. In some aspects, Reactive Composition G comprises about 3.1 wt % triacetin.

In some aspects, Reactive Composition G comprises about 0.1 wt % to about 1.9 wt % calcium stearate. In some aspects, Reactive Composition G comprises about 0.9 wt % calcium stearate.

In some aspects, Reactive Composition G comprises about 13.6 wt % to about 15.6 wt % HA/β-TCP granules. In some aspects, Reactive Composition G comprises about 14.6 wt % HA/β-TCP granules.

In some aspects, Reactive Composition G comprises about 64.4 wt % to about 66.4 wt % β-TCP powder. In some aspects, Reactive Composition G comprises about 65.4 wt % β-TCP powder.

In some aspects, Reactive Composition G comprises about 80 wt % of calcium phosphate or a calcium phosphate-based compound (e.g., calcium phosphate, a calcium phosphate derivate, β-TCP, HA/β-TCP, or a combination thereof).

Accordingly, in some aspects, Reactive Composition G comprises, consists of, or consists essentially of about 3.6 wt % to about 5.6 wt % ALD, about 6.6 wt % to about 8.6 wt % PCL, about 0.1 wt % to about 1.2 wt % BDO, about 2.5 wt % to about 4.5 wt % tocopherol acetate, about 2.1 wt % to about 4.1 wt % triacetin, about 0.1 wt % to about 1.9 wt % calcium stearate, about 13.6 wt % to about 15.6 wt % HA/β-TCP granules, and about 64.4 wt % to about 66.4 wt % β-TCP powder.

Accordingly, in some aspects, Reactive Composition G comprises, consists of, or consists essentially of about 4.6 wt % ALD, about 7.6 wt % PCL, about 0.2 wt % BDO, about 3.5 wt % tocopherol acetate, about 3.1 wt % triacetin, about 0.9 wt % calcium stearate, about 14.6 wt % HA/β-TCP granules, and about 65.4 wt % β-TCP powder.

In some aspects, Reactive Composition G is a putty.

In some aspects, Reactive Composition G comprises a pre-polymer formed from the reaction between isocyanate groups and polyol groups. In some aspects, Reactive Composition G comprises a percentage of reacted and unreacted isocyanate and/or reacted and unreacted polyol. In some aspects, Reactive Composition G comprises about 1.7 wt % of reacted prepolymer polyol. In some aspects, Reactive Composition G comprises about 5.9 wt % of unreacted prepolymer polyol. In some aspects, Reactive Composition G comprises about 1.7 wt % of reacted total polyol. In some aspects, Reactive Composition G comprises about 6.2 wt % of unreacted total polyol.

As would be understood in the art, the reacted percent can also be expressed as a percentage of the total isocyanate (i.e., —NCO) or hydroxyl (i.e., —OH) functional groups. In some aspects, Reactive Composition G comprises about 21.0% reacted hydroxyl groups. In some aspects, Reactive Composition G comprises about 79.0% unreacted hydroxyl groups.

Reactive Composition H

The present disclosure provides a reactive composition referred to herein as reactive "Reactive Composition H."

In some aspects, Reactive Composition H comprises about 38.7 wt % to about 40.7 wt % ALD. In some aspects, Reactive Composition H comprises about 39.7 wt % ALD.

In some aspects, Reactive Composition H comprises about 6.2 wt % to about 8.2 wt % tocopherol acetate. In some aspects, Reactive Composition H comprises about 7.2 wt % tocopherol acetate.

In some aspects, Reactive Composition H comprises about 0.01 wt % to about 1.1 wt % calcium stearate. In some aspects, Reactive Composition H comprises about 0.1 wt % calcium stearate.

In some aspects, Reactive Composition H comprises about 6.1 wt % to about 8.1 wt % β-TCP powder. In some aspects, Reactive Composition H comprises about 7.1 wt % β-TCP powder.

In some aspects, Reactive Composition H comprises about 39.1 wt % to about 41.1 wt % HA powder. In some aspects, Reactive Composition H comprises about 40.1 wt % HA powder.

In some aspects, Reactive Composition H comprises about 47.2 wt % of calcium phosphate or a calcium phosphate-based compound (e.g., calcium phosphate, a calcium phosphate derivate, β-TCP, HA/β-TCP, or a combination thereof).

12

In some aspects, Reactive Composition H comprises about 4.8 wt % to about 6.8 wt % barium sulfate. In some aspects, Reactive Composition H comprises about 5.8 wt % barium sulfate.

Accordingly, in some aspects, Reactive Composition H comprises, consists of, or consists essentially of about 38.7 wt % to about 40.7 wt % ALD, about 6.2 wt % to about 8.2 wt % tocopherol acetate, about 0.01 wt % to about 1.1 wt % calcium stearate, about 6.1 wt % to about 8.1 wt % β-TCP powder, about 39.1 wt % to about 41.1 wt % HA powder, and about 4.8 wt % to about 6.8 wt % barium sulfate.

Accordingly, in some aspects, Reactive Composition H comprises, consists of, or consists essentially of about 39.7 wt % ALD, about 7.2 wt % tocopherol acetate, about 0.1 wt % calcium stearate, about 7.1 wt %-TCP powder, about 40.1 wt % HA powder, and about 5.8 wt % barium sulfate.

In some aspects, Reactive Composition H is a paste.

In some aspects, Reactive Composition H comprises a pre-polymer formed from the reaction between isocyanate groups and polyol groups. In some aspects, Reactive Composition H comprises a percentage of reacted and unreacted isocyanate and/or reacted and unreacted polyol. In some aspects, Reactive Composition H comprises about 0 wt % of reacted isocyanate. In some aspects, Reactive Composition H comprises about 39.7 wt % of unreacted isocyanate.

As would be understood in the art, the reacted percent can also be expressed as a percentage of the total isocyanate (i.e., —NCO) or hydroxyl (i.e., —OH) functional groups. In some aspects, Reactive Composition H comprises about 0% reacted isocyanate groups. In some aspects, Reactive Composition H comprises about 100% unreacted isocyanate groups.

Reactive Composition I

The present disclosure provides a reactive composition referred to herein as reactive "Reactive Composition I."

In some aspects, Reactive Composition I comprises about 0.1 wt % to about 2 wt % ALD. In some aspects, Reactive Composition I comprises about 1 wt % ALD.

In some aspects, Reactive Composition I comprises about 30.1 wt % to about 32.1 wt % PCL. In some aspects, Reactive Composition I comprises about 31.1 wt % PCL.

In some aspects, Reactive Composition I comprises about 0.1 wt % to about 1.9 wt % BDO. In some aspects, Reactive Composition I comprises about 0.9 wt % BDO.

In some aspects, Reactive Composition I comprises about 4.4 wt % to about 6.4 wt % TEA. In some aspects, Reactive Composition I comprises about 5.4 wt % TEA.

In some aspects, Reactive Composition I comprises about 0.1 wt % to about 1.2 wt % triacetin. In some aspects, Reactive Composition I comprises about 0.2 wt % triacetin.

In some aspects, Reactive Composition I comprises about 0.9 wt % to about 2.9 wt % calcium stearate. In some aspects, Reactive Composition I comprises about 1.9 wt % calcium stearate.

In some aspects, Reactive Composition I comprises about 55.8 wt % to about 57.8.6 wt % HA powder. In some aspects, Reactive Composition I comprises about 56.8 wt % HA powder.

In some aspects, Reactive Composition I comprises about 56.8 wt % of calcium phosphate or a calcium phosphate-based compound (e.g., calcium phosphate, a calcium phosphate derivate, β-TCP, HA/β-TCP, or a combination thereof).

In some aspects, Reactive Composition I comprises about 1.8 wt % to about 3.8 wt % barium sulfate. In some aspects, Reactive Composition I comprises about 2.8 wt % barium sulfate.

Accordingly, in some aspects, Reactive Composition I comprises, consists of, or consists essentially of about 0.1 wt % to about 2 wt % ALD, about 30.1 wt % to about 32.1 wt % PCL, about 0.1 wt % to about 1.9 wt % BDO, about 4.4 wt % to about 6.4 wt % TEA, about 0.1 wt % to about 1.2 wt % triacetin, about 0.9 wt % to about 2.9 wt % calcium stearate, about 55.8 wt % to about 57.8.6 wt % HA powder, and about 1.8 wt % to about 3.8 wt % barium sulfate.

Accordingly, in some aspects, Reactive Composition I comprises, consists of, or consists essentially of about 1 wt % ALD, about 31.1 wt % PCL, about 0.9 wt % BDO, about 5.4 wt % TEA, about 0.2 wt % triacetin, about 1.9 wt % calcium stearate, about 56.8 wt % HA powder, and about 2.8 wt % barium sulfate.

In some aspects, Reactive Composition I is a paste.

In some aspects, Reactive Composition I comprises a pre-polymer formed from the reaction between isocyanate groups and polyol groups. In some aspects, Reactive Composition I comprises a percentage of reacted and unreacted isocyanate and/or reacted and unreacted polyol. In some aspects, Reactive Composition I comprises about 0.4 wt % of reacted prepolymer polyol. In some aspects, Reactive Composition I comprises about 30.7 wt % of unreacted prepolymer polyol. In some aspects, Reactive Composition I comprises about 0.3 wt % of reacted total polyol. In some aspects, Reactive Composition I comprises about 37.1 wt % of unreacted total polyol.

As would be understood in the art, the reacted percent can also be expressed as a percentage of the total isocyanate (i.e., —NCO) or hydroxyl (i.e., —OH) functional groups. In some aspects, Reactive Composition I comprises about 0.9% reacted hydroxyl groups. In some aspects, Reactive Composition I comprises about 99.1% unreacted hydroxyl groups.

Reactive Composition J

The present disclosure provides a reactive composition referred to herein as reactive "Reactive Composition J."

In some aspects, Reactive Composition J comprises about 27.3 wt % to about 29.3 wt % TMPI. In some aspects, Reactive Composition J comprises about 28.3 wt % TMPI.

In some as aspects, Reactive Composition J comprises about 2.3 wt % to about 4.3 wt % of TMPE. In some aspects, Reactive Composition J comprises about 2.3 wt % to about 4.3 wt % TMPE450. In some aspects, Reactive Composition J comprises about 3.3 wt % TMPE450. In some aspects, Reactive Composition J comprises about 3.3 wt % TMPE.

In some aspects, Reactive Composition J comprises about 1.9 wt % to about 3.9 wt % tocopherol acetate. In some aspects, Reactive Composition J comprises about 2.9 wt % tocopherol acetate.

In some aspects, Reactive Composition J comprises about 3.2 wt % to about 5.2 wt % paraffin oil. In some aspects, Reactive Composition J comprises about 4.2 wt % paraffin oil.

In some aspects, Reactive Composition J comprises about 28.2 wt % to about 30.2 wt % HA/β-TCP granules. In some aspects, Reactive Composition J comprises about 29.2 wt % HA/β-TCP granules.

In some aspects, Reactive Composition J comprises about 31.1 wt % to about 33.1 wt % β-TCP powder. In some aspects, Reactive Composition J comprises about 32.1 wt % β-TCP powder.

In some aspects, Reactive Composition J comprises about 61.3 wt % of calcium phosphate or a calcium phosphate-based compound (e.g., calcium phosphate, a calcium phosphate derivate, β-TCP, HA/β-TCP, or a combination thereof).

Accordingly, in some aspects, Reactive Composition J comprises, consists of, or consists essentially of about 27.3 wt % to about 29.3 wt % TMPI, about 2.3 wt % to about 4.3 wt % TMPE450 (or about 2.3 wt % to about 4.3 wt % TMPE), about 1.9 wt % to about 3.9 wt % tocopherol acetate, about 3.2 wt % to about 5.2 wt % paraffin oil, about 28.2 wt % to about 30.2 wt % HA/β-TCP granules, and about 31.1 wt % to about 33.1 wt % β-TCP powder.

Accordingly, in some aspects, Reactive Composition J comprises, consists of, or consists essentially of about 28.3 wt % TMPI, about 3.3 wt % TMPE450 (or about 3.3 wt % TMPE), about 2.9 wt % tocopherol acetate, about 4.2 wt % paraffin oil, about 29.2 wt % HA/β-TCP granules, and about 32.1 wt % β-TCP powder.

In some aspects, Reactive Composition J is a putty.

In some aspects, Reactive Composition J comprises a pre-polymer formed from the reaction between isocyanate groups and polyol groups. In some aspects, Reactive Composition J comprises a percentage of reacted and unreacted isocyanate and/or reacted and unreacted polyol. In some aspects, Reactive Composition J comprises about 3.6 wt % of reacted isocyanate. In some aspects, Reactive Composition J comprises about 24.7 wt % of unreacted isocyanate.

As would be understood in the art, the reacted percent can also be expressed as a percentage of the total isocyanate (i.e., —NCO) or hydroxyl (i.e., —OH) functional groups. In some aspects, Reactive Composition J comprises about 12.6% reacted isocyanate groups. In some aspects, Reactive Composition J comprises about 87.4% unreacted isocyanate groups.

Reactive Composition K

The present disclosure provides a reactive composition referred to herein as reactive "Reactive Composition K."

In some aspects, Reactive Composition K comprises about 2.9 wt % to about 4.9 wt % TMPI. In some aspects, Reactive Composition K comprises about 3.9 wt % TMPI.

In some aspects, Reactive Composition K comprises about 0.1 wt % to about 1.7 wt % TEA. In some aspects, Reactive Composition K comprises about 0.7 wt % TEA.

In some aspects, Reactive Composition K comprises about 2.9 wt % to about 4.9 wt % TMPE. In some aspects, Reactive Composition K comprises about 2.9 wt % to about 4.9 wt % TMPE170. In some aspects, Reactive Composition K comprises about 3.9 wt % TMPE170. In some aspects, Reactive Composition K comprises about 3.9 wt % TMPE.

In some aspects, Reactive Composition K comprises about 8.8 wt % to about 10.8 wt % TKP. In some aspects, Reactive Composition K comprises about 9.8 wt % TKP.

In some aspects, Reactive Composition K comprises about 6.5 wt % to about 8.5 wt % tocopherol acetate. In some aspects, Reactive Composition K comprises about 7.5 wt % tocopherol acetate.

In some aspects, Reactive Composition K comprises about 2.7 wt % to about 4.7 wt % triacetin. In some aspects, Reactive Composition K comprises about 3.7 wt % triacetin.

In some aspects, Reactive Composition K comprises about 0.1 wt % to about 2 wt % paraffin oil. In some aspects, Reactive Composition K comprises about 1 wt % paraffin oil.

In some aspects, Reactive Composition K comprises about 68.5 wt % to about 70.5 wt % HA powder. In some aspects, Reactive Composition K comprises about 69.5 wt % HA powder.

In some aspects, Reactive Composition K comprises about 69.5 wt % of calcium phosphate or a calcium phosphate-based compound (e.g., calcium phosphate, a calcium phosphate derivate, β-TCP, HA/β-TCP, or a combination thereof).

Accordingly, in some aspects, Reactive Composition K comprises, consists of, or consists essentially of about 2.9 wt % to about 4.9 wt % TMPI, about 0.1 wt % to about 1.7 wt % TEA, about 2.9 wt % to about 4.9 wt % TMPE170 (or about 2.9 wt % to about 4.9 wt % TMPE), about 8.8 wt % to about 10.8 wt % TKP, about 6.5 wt % to about 8.5 wt % tocopherol acetate, about 2.7 wt % to about 4.7 wt % triacetin, about 0.1 wt % to about 2 wt % paraffin oil, and about 68.5 wt % to about 70.5 wt % HA powder.

Accordingly, in some aspects, Reactive Composition K comprises, consists of, or consists essentially of about 3.9 wt % TMPI, about 0.7 wt % TEA, about 3.9 wt % TMPE170 (or about 3.9 wt % TMPE), about 9.8 wt % TKP, about 7.5 wt % tocopherol acetate, about 3.7 wt % triacetin, about 1 wt % paraffin oil, and about 69.5 wt % HA powder.

In some aspects, Reactive Composition K is a putty.

In some aspects, Reactive Composition K comprises a pre-polymer formed from the reaction between isocyanate groups and polyol groups. In some aspects, Reactive Composition K comprises a percentage of reacted and unreacted isocyanate and/or reacted and unreacted polyol. In some aspects, Reactive Composition K comprises about 1.8 wt % of reacted prepolymer polyol. In some aspects, Reactive Composition K comprises about 8.0 wt % of unreacted prepolymer polyol. In some aspects, Reactive Composition K comprises about 1.6 wt % of reacted total polyol. In some aspects, Reactive Composition K comprises about 12.8 wt % of unreacted total polyol.

As would be understood in the art, the reacted percent can also be expressed as a percentage of the total isocyanate (i.e., —NCO) or hydroxyl (i.e., —OH) functional groups. In some aspects, Reactive Composition K comprises about 11.1% reacted hydroxyl groups. In some aspects, Reactive Composition K comprises about 88.9% unreacted hydroxyl groups.

Reactive Composition L

The present disclosure provides a reactive composition referred to herein as reactive "Reactive Composition L."

In some aspects, Reactive Composition L comprises about 5.8 wt % to about 7.8 wt % ALD. In some aspects, Reactive Composition L comprises about 6.8 wt % ALD.

In some aspects, Reactive Composition L comprises about 4.2 wt % to about 6.2 wt % PCL. In some aspects, Reactive Composition L comprises about 5.2 wt % PCL.

In some aspects, Reactive Composition L comprises about 0.9 wt % to about 2.9 wt % BDO. In some aspects, Reactive Composition L comprises about 1.9 wt % BDO.

In some aspects, Reactive Composition L comprises about 2.7 wt % to about 4.7 wt % tocopherol acetate. in some aspects, Reactive Composition L comprises about 3.7 wt % tocopherol acetate.

In some aspects, Reactive Composition L comprises about 1.2 wt % to about 3.2 wt % triacetin. In some aspects, Reactive Composition L comprises about 2.2 wt % triacetin.

In some aspects, Reactive Composition L comprises about 0.1 wt % to about 1.5 wt % calcium stearate. In some aspects, Reactive Composition L comprises about 0.5 wt % calcium stearate.

In some aspects, Reactive Composition L comprises about 18 wt % to about 20 wt % HA/β-TCP granules. In some aspects, Reactive Composition L comprises about 19 wt % HA/β-TCP granules.

In some aspects, Reactive Composition L comprises about 58 wt % to about 60 wt % β-TCP powder. In some aspects, Reactive Composition L comprises about 59 wt % β-TCP powder.

In some aspects, Reactive Composition L comprises about 78 wt % of calcium phosphate or a calcium phosphate-based compound (e.g., calcium phosphate, a calcium phosphate derivate, β-TCP, HA/β-TCP, or a combination thereof).

In some aspects, Reactive Composition L comprises about 0.7 wt % to about 2.7 wt % gentamicin. In some aspects, Reactive Composition L comprises about 1.7% gentamicin.

Accordingly, in some aspects, Reactive Composition L comprises, consists of, or consists essentially of about 5.8 wt % to about 7.8 wt % ALD, about 4.2 wt % to about 6.2 wt % PCL, about 0.9 wt % to about 2.9 wt % BDO, about 2.7 wt % to about 4.7 wt % tocopherol acetate, about 1.2 wt % to about 3.2 wt % triacetin, about 0.1 wt % to about 1.5 wt % calcium stearate, about 18 wt % to about 20 wt % HA/β-TCP granules, about 58 wt % to about 60 wt % β-TCP powder, and about 0.7 wt % to about 2.7 wt % gentamicin.

Accordingly, in some aspects, Reactive Composition L comprises, consists of, or consists essentially of about 6.8 wt % ALD, about 5.2 wt % PCL, about 1.9 wt % BDO, about 3.7 wt % tocopherol acetate, about 2.2 wt % triacetin, about 0.5 wt % calcium stearate, about 19 wt % HA/β-TCP granules, about 59 wt % β-TCP powder, and about 1.7 wt % gentamicin.

In some aspects, Reactive Composition L is a putty.

Reactive Composition M

The present disclosure provides a reactive composition referred to herein as reactive "Reactive Composition M."

In some aspects, Reactive Composition M comprises about 5.8 wt % to about 7.8 wt % ALD. In some aspects, Reactive Composition M comprises about 6.8 wt % ALD.

In some aspects, Reactive Composition M comprises about 4.2 wt % to about 6.2 wt % PCL. In some aspects, Reactive Composition M comprises about 5.2 wt % PCL.

In some aspects, Reactive Composition M comprises about 0.9 wt % to about 2.9 wt % BDO. In some aspects, Reactive Composition M comprises about 1.9 wt % BDO.

In some aspects, Reactive Composition M comprises about 2.7 wt % to about 4.7 wt % tocopherol acetate. in some aspects, Reactive Composition M comprises about 3.7 wt % tocopherol acetate.

In some aspects, Reactive Composition M comprises about 1.2 wt % to about 3.2 wt % triacetin. In some aspects, Reactive Composition M comprises about 2.2 wt % triacetin.

In some aspects, Reactive Composition M comprises about 0.1 wt % to about 1.5 wt % calcium stearate. In some aspects, Reactive Composition M comprises about 0.5 wt % calcium stearate.

In some aspects, Reactive Composition M comprises about 18 wt % to about 20 wt % HA/β-TCP granules. In some aspects, Reactive Composition M comprises about 19 wt % HA/β-TCP granules.

In some aspects, Reactive Composition M comprises about 58 wt % to about 60 wt % β-TCP powder. In some aspects, Reactive Composition M comprises about 59 wt % β-TCP powder.

In some aspects, Reactive Composition M comprises about 78 wt % of calcium phosphate or a calcium phosphate-based compound (e.g., calcium phosphate, a calcium phosphate derivate, β-TCP, HA/β-TCP, or a combination thereof).

In some aspects, Reactive Composition M comprises about 0.7 wt % to about 2.7 wt % tobramycin. In some aspects, Reactive Composition M comprises about 1.7% tobramycin.

Accordingly, in some aspects, Reactive Composition M comprises, consists of, or consists essentially of about 5.8 wt % to about 7.8 wt % ALD, about 4.2 wt % to about 6.2 wt % PCL, about 0.9 wt % to about 2.9 wt % BDO, about 2.7 wt % to about 4.7 wt % tocopherol acetate, about 1.2 wt % to about 3.2 wt % triacetin, about 0.1 wt % to about 1.5 wt % calcium stearate, about 18 wt % to about 20 wt % HA/β-TCP granules, about 58 wt % to about 60 wt % β-TCP powder, and about 0.7 wt % to about 2.7 wt % tobramycin.

Accordingly, in some aspects, Reactive Composition M comprises, consists of, or consists essentially of about 6.8 wt % ALD, about 5.2 wt % PCL, about 1.9 wt % BDO, about 3.7 wt % tocopherol acetate, about 2.2 wt % triacetin, about 0.5 wt % calcium stearate, about 19 wt % HA/β-TCP granules, about 59 wt % β-TCP powder, and about 1.7 wt % tobramycin.

In some aspects, Reactive Composition M is a putty.
Reactive Composition N

The present disclosure provides a reactive composition referred to herein as reactive "Reactive Composition N."

In some aspects, Reactive Composition N comprises about 4.3 wt % to about 6.3 wt % ALD. In some aspects, Reactive Composition N comprises about 5.3 wt % ALD.

In some aspects, Reactive Composition N comprises about 4 wt % to about 6 wt % PCL. In some aspects, Reactive Composition N comprises about 5 wt % PCL.

In some aspects, Reactive Composition N comprises about 0.8 wt % to about 2.8 wt % BDO. In some aspects, Reactive Composition N comprises about 1.8 wt % BDO.

In some aspects, Reactive Composition N comprises about 2.6 wt % to about 4.6 wt % tocopherol acetate. in some aspects, Reactive Composition N comprises about 3.6 wt % tocopherol acetate.

In some aspects, Reactive Composition N comprises about 1.1 wt % to about 3.1 wt % triacetin. In some aspects, Reactive Composition N comprises about 2.1 wt % triacetin.

In some aspects, Reactive Composition N comprises about 0.1 wt % to about 1.5 wt % calcium stearate. In some aspects, Reactive Composition N comprises about 0.5 wt % calcium stearate.

In some aspects, Reactive Composition N comprises about 17.3 wt % to about 19.3 wt % HA/β-TCP granules. In some aspects, Reactive Composition N comprises about 18.3 wt % HA/β-TCP granules.

In some aspects, Reactive Composition N comprises about 55.9 wt % to about 57.9 wt % β-TCP powder. In some aspects, Reactive Composition N comprises about 56.9 wt % β-TCP powder.

In some aspects, Reactive Composition N comprises about 75.2 wt % of calcium phosphate or a calcium phosphate-based compound (e.g., calcium phosphate, a calcium phosphate derivate, β-TCP, HA/β-TCP, or a combination thereof).

In some aspects, Reactive Composition N comprises about 5.4 wt % to about 7.4 wt % vancomycin. In some aspects, Reactive Composition N comprises about 6.4% vancomycin.

Accordingly, in some aspects, Reactive Composition N comprises, consists of, or consists essentially of about 4.3 wt % to about 6.3 wt % ALD, about 4 wt % to about 6 wt % PCL, about 0.8 wt % to about 2.8 wt % BDO, about 2.6 wt % to about 4.6 wt % tocopherol acetate, about 1.1 wt % to about 3.1 wt % triacetin, about 0.1 wt % to about 1.5 wt % calcium stearate, about 17.3 wt % to about 19.3 wt % HA/β-TCP granules, about 55.9 wt % to about 57.9 wt % β-TCP powder, and about 5.4 wt % to about 7.4 wt % vancomycin.

Accordingly, in some aspects, Reactive Composition N comprises, consists of, or consists essentially of about 5.3 wt % ALD, about 5 wt % PCL, about 1.8 wt % BDO, about 3.6 wt % tocopherol acetate, about 2.1 wt % triacetin, about 0.5 wt % calcium stearate, about 18.3 wt % HA/β-TCP granules, about 56.9 wt % β-TCP powder, and about 6.4 wt % vancomycin.

In some aspects, Reactive Composition N is a putty.
Reactive Composition O

The present disclosure provides a reactive composition referred to herein as reactive "Reactive Composition O."

In some aspects, Reactive Composition O comprises about 4.2 wt % to about 6.2 wt % ALD. In some aspects, Reactive Composition O comprises about 5.2 wt % ALD.

In some aspects, Reactive Composition O comprises about 3.9 wt % to about 5.9 wt % PCL. In some aspects, Reactive Composition O comprises about 4.9 wt % PCL.

In some aspects, Reactive Composition O comprises about 0.8 wt % to about 2.8 wt % BDO. In some aspects, Reactive Composition O comprises about 1.8 wt % BDO.

In some aspects, Reactive Composition O comprises about 2.5 wt % to about 4.5 wt % tocopherol acetate. in some aspects, Reactive Composition O comprises about 3.5 wt % tocopherol acetate.

In some aspects, Reactive Composition O comprises about 1.1 wt % to about 3.1 wt % triacetin. In some aspects, Reactive Composition O comprises about 2.1 wt % triacetin.

In some aspects, Reactive Composition O comprises about 0.1 wt % to about 1.5 wt % calcium stearate. In some aspects, Reactive Composition O comprises about 0.5 wt % calcium stearate.

In some aspects, Reactive Composition O comprises about 17 wt % to about 19 wt % HA/β-TCP granules. In some aspects, Reactive Composition O comprises about 18 wt % HA/β-TCP granules.

In some aspects, Reactive Composition O comprises about 54.9 wt % to about 56.9 wt % β-TCP powder. In some aspects, Reactive Composition O comprises about 55.9 wt % β-TCP powder.

In some aspects, Reactive Composition O comprises about 73.9 wt % of calcium phosphate or a calcium phosphate-based compound (e.g., calcium phosphate, a calcium phosphate derivate, β-TCP, HA/β-TCP, or a combination thereof).

In some aspects, Reactive Composition O comprises about 5.4 wt % to about 7.4 wt % vancomycin. In some aspects, Reactive Composition O comprises about 6.4% vancomycin.

In some aspects, Reactive Composition O comprises about 0.7 wt % to about 2.7 wt % tobramycin or gentamycin. In some aspects, Reactive Composition O comprises about 1.7% tobramycin or gentamycin.

Accordingly, in some aspects, Reactive Composition O comprises, consists of, or consists essentially of about 4.2 wt % to about 6.2 wt % ALD, about 3.9 wt % to about 5.9 wt % PCL, about 0.8 wt % to about 2.8 wt % BDO, about 2.5 wt % to about 4.5 wt % tocopherol acetate, about 1.1 wt % to about 3.1 wt % triacetin, about 0.1 wt % to about 1.5 wt % calcium stearate, about 17 wt % to about 19 wt % HA/β-TCP granules, about 54.9 wt % to about 56.9 wt % β-TCP powder, about 5.4 wt % to about 7.4 wt % vancomycin, and about 0.7 wt % to about 2.7 wt % tobramycin or gentamycin.

Accordingly, in some aspects, Reactive Composition O comprises, consists of, or consists essentially of about 5.2 wt % ALD, about 4.9 wt % PCL, about 1.8 wt % BDO, about 3.5 wt % tocopherol acetate, about 2.1 wt % triacetin, about 0.5 wt % calcium stearate, about 18 wt % HA/β-TCP granules, about 55.9 wt % β-TCP powder, about 6.4 wt % vancomycin, and about 1.7 wt % tobramycin or gentamycin.

In some aspects, Reactive Composition O is a putty.

Composition A+B

The present disclosure provides methods comprising mixing Reactive Composition A and Reactive Composition B together to yield a composition herein referred to as "Composition A+B".

Accordingly, the present disclosure provides Composition A+B, wherein Composition A+B comprises, consists of, or consists essentially of about 19.5 wt % to about 21.5 wt % ALD, about 3 wt % to about 5 wt % PCL, about 0.1 wt % to about 2 wt % BDO, about 4.2 wt % to about 6.2 wt % tocopherol acetate, about 0.1 wt % to about 2.1 wt % triacetin, about 0.1 wt % to about 1.3 wt % calcium stearate, about 34.5 wt % to about 36.5 wt % HA/β-TCP granules, and about 31.5 wt % to about 33.5 wt % β-TCP powder.

In some aspects, Composition A+B can comprise, consist of, or consist essentially of about 20.5 wt % ALD, about 4 wt % PCL, about 1 wt % BDO, about 5.2 wt % tocopherol acetate, about 1.1 wt % triacetin, about 0.3 wt % calcium stearate, about 35.5 wt % HA/β-TCP granules, and about 32.5 wt %, β-TCP powder.

In some aspects, Reactive Composition A+B comprises about 68 wt % of calcium phosphate or a calcium phosphate-based compound (e.g., calcium phosphate, a calcium phosphate derivate, β-TCP, HA/β-TCP, or a combination thereof).

In some aspects, Composition A+B is absorbable.

Composition A+C

The present disclosure provides methods comprising mixing Reactive Composition A and Reactive Composition C together to yield a composition herein referred to as "Composition A+C".

Accordingly, the present disclosure provides Composition A+C, wherein Composition A+C comprises, consists of, or consists essentially of about 20.1 wt % to about 22.1 wt % ALD, about 2.3 wt % to about 5.3 wt % PCL, about 0.1 wt % to about 1.5 wt % BDO, about 0.2 wt % to about 2.2 wt % TEA, about 4.6 wt % to about 6.6 wt % tocopherol acetate, about 0.1 wt % to about 2 wt % triacetin, about 0.1 wt % to about 1.2 wt % calcium stearate, about 34.3 wt % to about 36.3 wt % HA/β-TCP granules, and about 30.8 wt % to about 32.8 wt %-TCP powder.

In some aspects, Composition A+C can comprise, consist of, or consist essentially of about 21.1 wt % ALD, about 3.3 wt % PCL, about 0.5 wt % BDO, about 1.2 wt % TEA, about 5.6 wt % tocopherol acetate, about 1 wt % triacetin, about 0.2 wt % calcium stearate, about 35.3 wt % HA/β-TCP granules, and about 31.8 wt %, β-TCP powder.

In some aspects, Reactive Composition A+C comprises about 67.1 wt % of calcium phosphate or a calcium phosphate-based compound (e.g., calcium phosphate, a calcium phosphate derivate, β-TCP, HA/β-TCP, or a combination thereof).

In some aspects, Composition A+C is absorbable.

Composition D+E

The present disclosure provides methods comprising mixing Reactive Composition D and Reactive Composition E together to yield a composition herein referred to as "Composition D+E".

Accordingly, the present disclosure provides Composition D+E, wherein Composition D+E comprises, consists of, or consists essentially of about 31.3 wt % to about 33.3 wt % ALD, about 4.6 wt % to about 6.6 wt % PCL, about 0.1 wt % to about 1.2 wt % BDO, about 0.6 wt % to about 2.6 wt % TEA, about 4.8 wt % to about 6.8 wt % tocopherol acetate, about 0.1 wt % to about 1.4 wt % calcium stearate, about 5.4 wt % to about 7.4 wt % β-TCP powder, and about 46.8 wt % to about 48.8 wt % HA powder.

Accordingly, the present disclosure provides Composition D+E, wherein Composition D+E comprises, consists of, or consists essentially of about 32.3 wt % ALD, about 5.6 wt % PCL, about 0.2 wt % BDO, about 1.6 wt % TEA, about 5.8 wt % tocopherol acetate, about 0.4 wt % calcium stearate, about 6.4 wt % β-TCP powder, and about 47.8 wt % HA powder.

In some aspects, Reactive Composition D+E comprises about 54.2 wt % of calcium phosphate or a calcium phosphate-based compound (e.g., calcium phosphate, a calcium phosphate derivate, β-TCP, HA/β-TCP, or a combination thereof).

In some aspects, Composition D+E is absorbable.

Composition F+G

The present disclosure provides methods comprising mixing Reactive Composition F and Reactive Composition G together to yield a composition herein referred to as "Composition F+G".

Accordingly, the present disclosure provides Composition F+G, wherein Composition F+G comprises, consists of, or consists essentially of about 16.4 wt % to about 18.4 wt % ALD, about 4 wt % to about 6 wt % PCL, about 0.01 wt % to about 1.1 wt % BDO, about 4.1 wt % to about 6.1 wt % tocopherol acetate, about 0.5 wt % to about 2.5 wt % triacetin, about 0.1 wt % to about 1.5 wt % calcium stearate, about 34.4 wt % to about 36.4 wt % HA/β-TCP granules, and about 33.9 wt % to about 35.9 wt % β-TCP powder.

Accordingly, the present disclosure provides Composition F+G, wherein Composition F+G comprises, consists of, or consists essentially of about 17.4 wt % ALD, about 5 wt % PCL, about 0.1 wt % BDO, about 5.1 wt % tocopherol acetate, about 1.5 wt % triacetin, about 0.5 wt % calcium stearate, about 35.4 wt % HA/β-TCP granules, and about 34.9 wt % β-TCP powder.

In some aspects, Reactive Composition F+G comprises about 70.3 wt % of calcium phosphate or a calcium phosphate-based compound (e.g., calcium phosphate, a calcium phosphate derivate, β-TCP, HA/β-TCP, or a combination thereof).

In some aspects, Composition F+G is absorbable.

Composition H+I

The present disclosure provides methods comprising mixing Reactive Composition H and Reactive Composition I together to yield a composition herein referred to as "Composition H+I".

Accordingly, the present disclosure provides Composition H+I, wherein Composition H+I comprises, consists of, or consists essentially of about 31.1 wt % to about 33.1 wt % ALD, about 5.1 wt % to about 7.1 wt % PCL, about 0.1 wt % to about 1.2 wt % BDO, about 0.1 wt % to about 2.1 wt % TEA, about 4.8 wt % to about 6.8 wt % tocopherol acetate, about 0.1 wt % to about 1.4 wt % calcium stearate, about 4.7 wt % to about 6.7 wt % β-TCP powder, about 42.4 wt % to about 44.4 wt % HA powder, and about 4.2 wt % to about 6.2 wt % barium sulfate.

Accordingly, the present disclosure provides Composition H+I, wherein Composition H+I comprises, consists of, or consists essentially of about 32.1 wt % ALD, about 6.1 wt % PCL, about 0.2 wt % BDO, about 1.1 wt % TEA, about 5.8 wt % tocopherol acetate, about 0.4 wt % calcium stearate, about 5.7 wt % β-TCP powder, about 43.4 wt % HA powder, and about 5.2 wt % barium sulfate.

In some aspects, Reactive Composition H+I comprises about 49.1 wt % of calcium phosphate or a calcium phosphate-based compound (e.g., calcium phosphate, a calcium phosphate derivate, β-TCP, HA/β-TCP, or a combination thereof).

In some aspects, Composition H+I is absorbable.

Composition J+K

The present disclosure provides methods comprising mixing Reactive Composition J and Reactive Composition K together to yield a composition herein referred to as "Composition J+K".

Accordingly, the present disclosure provides Composition J+K, wherein Composition J+K comprises, consists of, or consists essentially of about 16.9 wt % to about 18.9 wt % TMPI, about 0.1 wt % to about 1.3 wt % TEA, about 0.7 wt % to about 2.7 wt % TMPE170 (or about 0.7 wt % to about 2.7 wt % TMPE), about 0.9 wt % to about 2.9 wt % TMPE450 (or about 0.9 wt % to about 2.9 wt % TMPE), about 3.2 wt % to about 5.2 wt % TKP, about 3.8 wt % to about 5.8 wt % tocopherol acetate, about 0.6 wt % to about 2.6 wt % triacetin, about 1.9 wt % to about 3.9 wt % paraffin oil, about 15.7 wt % to about 17.7 wt % HA/β-TCP granules, about 17.4 wt % to about 19.4 wt % β-TCP powder, and about 28.8 wt % to about 30.8 wt % HA powder.

Accordingly, the present disclosure provides Composition J+K, wherein Composition J+K comprises, consists of, or consists essentially of about 17.9 wt % TMPI, about 0.3 wt % TEA, about 1.7 wt % TMPE170 (or about 1.7 wt % TMPE), about 1.9 wt % TMPE450 (or about 1.9 wt % TMPE), about 4.2 wt % TKP, about 4.8 wt % tocopherol acetate, about 1.6 wt % triacetin, about 2.9 wt % paraffin oil, about 16.7 wt % HA/β-TCP granules, about 18.4 wt % β-TCP powder, and about 29.8 wt % HA powder.

In some aspects, Reactive Composition J+K comprises about 64.9 wt % of calcium phosphate or a calcium phosphate-based compound (e.g., calcium phosphate, a calcium phosphate derivate, β-TCP, HA/β-TCP, or a combination thereof).

In some aspects, Composition J+K is non-absorbable.

Composition A+L

The present disclosure provides methods comprising mixing Reactive Composition A and Reactive Composition L together to yield a composition herein referred to as "Composition A+L".

Accordingly, the present disclosure provides Composition A+L, wherein Composition A+L comprises, consists of, or consists essentially of about 19.4 wt % to about 21.4 wt % ALD, about 3 wt % to about 5 wt % PCL, about 0.1 wt % to about 1.9 wt % BDO, about 4.1 wt % to about 6.1 wt % tocopherol acetate, about 0.1 wt % to about 2.1 wt % triacetin, about 0.1 wt % to about 1.3 wt % calcium stearate, about 34.4 wt % to about 36.4 wt % HA/β-TCP granules, about 31 wt % to about 33 wt % β-TCP powder, and about 0.1 wt % to about 1.8 wt % gentamicin.

In some aspects, Composition A+L can comprise, consist of, or consist essentially of about 20.4 wt % ALD, about 4 wt % PCL, about 0.9 wt % BDO, about 5.1 wt % tocopherol acetate, about 1.1 wt % triacetin, about 0.3 wt % calcium stearate, about 35.4 wt % HA/β-TCP granules, about 32 wt % β-TCP powder, and about 0.8 wt % gentamicin.

In some aspects, Reactive Composition A+L comprises about 67.4 wt % of calcium phosphate or a calcium phosphate-based compound (e.g., calcium phosphate, a calcium phosphate derivate, β-TCP, HA/β-TCP, or a combination thereof).

In some aspects, Composition A+L is absorbable.

Composition A+M

The present disclosure provides methods comprising mixing Reactive Composition A and Reactive Composition M together to yield a composition herein referred to as "Composition A+M".

Accordingly, the present disclosure provides Composition A+M, wherein Composition A+M comprises, consists of, or consists essentially of about 19.4 wt % to about 21.4 wt % ALD, about 3 wt % to about 5 wt % PCL, about 0.1 wt % to about 1.9 wt % BDO, about 4.1 wt % to about 6.1 wt % tocopherol acetate, about 0.1 wt % to about 2.1 wt % triacetin, about 0.1 wt % to about 1.3 wt % calcium stearate, about 34.4 wt % to about 36.4 wt % HA/β-TCP granules, about 31 wt % to about 33 wt % β-TCP powder, and about 0.1 wt % to about 1.8 wt % tobramycin.

In some aspects, Composition A+M can comprise, consist of, or consist essentially of about 20.4 wt % ALD, about 4 wt % PCL, about 0.9 wt % BDO, about 5.1 wt % tocopherol acetate, about 1.1 wt % triacetin, about 0.3 wt % calcium stearate, about 35.4 wt % HA/β-TCP granules, about 32 wt % β-TCP powder, and about 0.8 wt % tobramycin.

In some aspects, Reactive Composition A+M comprises about 67.4 wt % of calcium phosphate or a calcium phosphate-based compound (e.g., calcium phosphate, a calcium phosphate derivate, β-TCP, HA/β-TCP, or a combination thereof).

In some aspects, Composition A+M is absorbable.

Composition A+N

The present disclosure provides methods comprising mixing Reactive Composition A and Reactive Composition N together to yield a composition herein referred to as "Composition A+N".

Accordingly, the present disclosure provides Composition A+N, wherein Composition A+N comprises, consists of, or consists essentially of about 18.7 wt % to about 20.7 wt % ALD, about 2.9 wt % to about 4.9 wt % PCL, about 0.1 wt % to about 1.9 wt % BDO, about 4.1 wt % to about 6.1 wt % tocopherol acetate, about 0.1 wt % to about 2.1 wt % triacetin, about 0.1 wt % to about 1.3 wt % calcium stearate, about 34 wt % to about 36 wt % HA/β-TCP granules, about 29.9 wt % to about 31.9 wt % β-TCP powder, and about 2.2 wt % to about 4.2 wt % vancomycin.

In some aspects, Composition A+N can comprise, consist of, or consist essentially of about 19.7 wt % ALD, about 3.9 wt % PCL, about 0.9 wt % BDO, about 5.1 wt % tocopherol acetate, about 1.1 wt % triacetin, about 0.3 wt % calcium stearate, about 35 wt % HA/β-TCP granules, about 30.9 wt % β-TCP powder, and about 3.2 wt % vancomycin.

In some aspects, Reactive Composition A+N comprises about 65.9 wt % of calcium phosphate or a calcium phosphate-based compound (e.g., calcium phosphate, a calcium phosphate derivate, β-TCP, HA/β-TCP, or a combination thereof).

In some aspects, Composition A+N is absorbable.

Composition A+O

The present disclosure provides methods comprising mixing Reactive Composition A and Reactive Composition O together to yield a composition herein referred to as "Composition A+O".

Accordingly, the present disclosure provides Composition A+O, wherein Composition A+O comprises, consists of, or consists essentially of about 18.7 wt % to about 20.7 wt % ALD, about 2.8 wt % to about 4.8 wt % PCL, about 0.1 wt % to about 1.9 wt % BDO, about 4 wt % to about 6 wt % tocopherol acetate, about 0.1 wt % to about 2.1 wt % triacetin, about 0.1 wt % to about 1.3 wt % calcium stearate, about 33.9 wt % to about 35.9 wt % HA/β-TCP granules, about 29.4 wt % to about 31.4 wt % β-TCP powder, about 2.2 wt % to about 4.2 wt % vancomycin, and about 0.1% to about 1.8% tobramycin or gentamycin.

In some aspects, Composition A+O can comprise, consist of, or consist essentially of about 19.7 wt % ALD, about 3.8 wt % PCL, about 0.9 wt % BDO, about 5 wt % tocopherol acetate, about 1.1 wt % triacetin, about 0.3 wt % calcium stearate, about 34.9 wt % HA/β-TCP granules, about 30.4 wt % β-TCP powder, about 3.2 wt % vancomycin, and about 0.8% tobramycin or gentamycin.

In some aspects, Reactive Composition A+O comprises about 65.3 wt % of calcium phosphate or a calcium phosphate-based compound (e.g., calcium phosphate, a calcium phosphate derivate, β-TCP, HA/β-TCP, or a combination thereof).

In some aspects, Composition A+O is absorbable.

Additives to the Compositions of the Present Disclosure

Any of the compositions (e.g. reactive compositions) can further comprise one or more additional additives.

In some aspects, an additive is an antibiotic. Non-limiting examples of antibiotics include beta-lactam antibiotics such as tobramycin, subclasses Penicillins (examples: penicillin G, methicillin, oxacillin, ampicillin, amoxicillin), Cephalosporins, Glycopeptides (example vancomycin), Carbapenems (examples imipenem and meropenem), Polymyxin and Bacitracins (example bacitracin, neomycin) or Lipopeptides (example daptomycin), Protein synthesis inhibitors such as subclasses Aminoglycosides (example gentamicin, streptomycin, kanamycin), Tetracyclines (examples tetracycline, doxycycline, minocycline, and tigecycline), Oxazilodinone (linezolid), Peptidyl transferases (example Chloramphenicol), Macrolides (examples erythromycin, azithromycin, telithromycin), Lincosamides (examples clindamycin), and Streptogramins (example prisintamycin), DNA synthesis inhibitors such as metronidazole and subclass Fluoroquinolones (examples ciprofloxacin, norfloxacin, morifloxacin), RNA synthesis inhibitors such as rifampin, Mycolic acid synthesis inhibitors such as isoniazid, and Folic acid synthesis inhibitors such as Trimethoprim and subclass Sulfonamides (examples sulfamethoxazole, sulfadoxin).

In some aspects, an antibiotic is present in an amount ranging from about 0.01 wt % to about 8 wt % of the composition.

In some aspects, an antibiotic is gentamicin. Gentamicin can be present at a concentration from about 10 mg/cc to about 200 mg/cc of a composition. Gentamicin can be present from about 0.7 wt % to about 2.7 wt % of a composition. Gentamicin can be present from about 0.1 wt % to about 1.8 wt % of a composition. Gentamicin can be present at about 1.7 wt % of a composition. Gentamicin can be present at about 0.8% wt %.

In some aspects, an antibiotic is vancomycin. Vancomycin can be present from about 40 mg/cc to about 600 mg/cc of a composition. Vancomycin can be present from about 5.4% to about 7.4% of a composition. Vancomycin can be present from about 2.2 wt % to about 4.2 wt % of a composition. Vancomycin can be present at about 6.4 wt % of a composition. Vancomycin can be present at about 3.2 wt %.

In some aspects, an antibiotic is minocycline. Minocycline can be present from about 5 mg/cc to about 200 mg/cc of a composition.

In some aspects, an antibiotic is rifampin. Rifampin can be present from about 10 mg/cc to about 300 mg/cc of composition.

In some aspects, an antibiotic is tobramycin. Tobramycin can be present from about 0.7 wt % to about 2.7 wt % of a composition. Tobramycin can be present from about 0.1 wt % to about 1.8 wt % of a composition. Tobramycin can be present at about 1.7 wt % of a composition. Tobramycin can be present at about 0.8% wt %.

In some aspects, an additive is an anesthetic. Non-limiting examples of anesthetics include lidocaine, bupivacaine, tetracaine, and ropivacaine, including the freebases, their salts, and derivatives thereof.

In some aspects, an additive is an antioxidants. Non-limiting examples of suitable antioxidants include Vitamin E acetate, IRGANOX 1010 and IRGANOX 1035 (Ciba Geigy), and CYANOX 1790 and CYANOX 2777 (Cytec Industries). In some aspects, an antioxidant is present in an amount ranging from about 0.01 wt % to about 5 wt % of a composition.

In some aspects, an additive is a steroid-based compound, such as an intracellular messenger, to modulate the rate of bone growth.

In some aspects, an additive can be a plurality of progenitor cells.

In some aspects, an additive can be a "cell opener". Non-limiting examples of cell openers as described herein include ORTOGEL501 (Goldschmidt) and X-AIR (Specialty Polymers & Services). In some aspects, cell openers can be present in an amount from about 0.1 wt % to about 5 wt % of a composition. In some aspects, the cell openers can be present in amounts of about 1 wt % to about 2 wt %. In some aspects, the cell openers can be present in amounts of about 1 wt % to about 3 wt % of a composition.

In some aspects, an additive can be an active chemical hemostats. Non-limiting examples of active chemical hemostats include, but are not limited to, prothrombin, thrombin, fibrinogen, and fibrin.

In some aspects an additive can be epinephrine, tannic acid, ferrous sulfate, and/or the double-sulfates of a trivalent metal and a univalent metal such as potassium aluminum sulfate and ammonium aluminum sulfate.

In some aspects, an additive can be an osteoconductive additive. Non-limiting examples of osteoconductive additives include, but are not limited to, carbonate (e.g., calcium carbonate, magnesium carbonate, aluminum carbonate, iron carbonate, zinc carbonate, calcium bicarbonate, and sodium bicarbonate), bone (e.g., demineralized bone matrix, bone morphogenetic protein, allograft bone, and/or autologous bone), calcium phosphate, siliconized calcium phosphate, substituted calcium phosphates (e.g., with magnesium, strontium, or silicate), calcium pyrophosphate glass, calcium sulfate, tricalcium phosphate (e.g., β-tricalcium phosphate), or any combination thereof.

In some aspects, an additive can be a surfactant. Non-limiting examples of surfactants include, but are not limited to, DABCO DC 193 and DABCO DC 5241 (Air Products, Inc.), MAXEMUL 6106 (Uniqema), and silicone surfactants (e.g., those available from Struktol Corp.).

In some aspects, an additive can be a radiopaque material that imparts radiopacity to a composition of the present disclosure. Non-limiting examples of a radiopaque substance include ceramic particles (e.g., calcium phosphate), barium sulfate ($BaSO_4$), and zirconium dioxide ($ZrO_2$). Examples of commercially available radiopaque substances include LIPIODOL, HYPAQUE, and OMNIPAQUE.

In some aspects, the compositions of the present disclosure contain no added water. In some aspects, the compositions of the present disclosure are anhydrous. In some aspects of the compositions of the present disclosure, wherein there is no added water in the compositions, water may nevertheless be present in small amounts. In some aspects, the compositions of the present disclosure are formulated in an atmosphere that contains moisture resulting in the incorporation of water into the compositions. In some aspects, the compositions of the present disclosure are prepared under a nitrogen purge that comprises a desired amount of moisture, thereby controlling the water content of the compositions. In other aspects, water may be added to the compositions during the process of their formation from the component parts. In other aspects, the compositions are prepared under essentially water-free conditions with anhydrous components such that the resulting compositions are essentially anhydrous.

In some aspects of the compositions of the present disclosure water is present in the compositions being made in an amount from at least 0.01 wt % to 3 wt % of the composition. In certain aspects, water is present in an amount ranging from 0.05 wt % to 1 wt %, from 0.05 wt % to 1.5 wt %, from 0.1 wt % to 1 wt %, from 0.1 wt % to 1.5 wt %, from 0.1 wt % to 2 wt %, from 1 wt % to 2 wt %, or from 2 wt % to 3 wt %.

Characteristics of Compositions of the Present Disclosure

In some aspects, the compositions of the present disclosure are osteoconductive. The term "osteoconductive" as used throughout herein, indicates that the compositions of the present disclosure supports the attachment and proliferation of osteocytes/osteoblasts.

In some aspects, the compositions of the present disclosure support the attachment and growth of bone on its surface.

In some aspects, the compositions of the present disclosure are hemostatic compositions. The term hemostatic composition as used throughout herein, means that the compositions of the present disclosure are able to be applied to the surface of bleeding bone in its uncured/unset state, and are able to cease bone bleeding upon application to the bone tissue. In some aspects, the hemostatic compositions of the present disclosure are adhesive and capable of adhering to bone tissue. In some aspects, the hemostasis caused by the compositions of the present disclosure is mechanical (tamponade). In some aspects, the hemostasis caused by the compositions of the present disclosure is chemical.

Without wishing to be bound by theory, the composition of the present disclosure can exhibit one or more improved properties as compared to bone-related compositions known in the art. These superior properties include, but are not limited to: improved control of phase separation; improved shelf-life; improved ability to be sterilized using gamma sterilization without degradation; improved hydrophobicity/hydrophilicity range to resist rapid dissolution and heavy irrigation/bleeding while still allowing for polymer degradation; improved ability limit radiation leaks; improved rates of polymerization to facilitate re-incorporation and delivery; improved exothermic reaction qualities for improved handling and tissue health; improved polymer balance to allow for improved mixing and adhering properties; improved expansion qualities; improved control of porosity; improved radiopacity; improved ability to visualize with standard imaging; improved particle sizes to mask polymer and create space and benefits; improved release profiles of component additives, including extended release; improved durability (particles less likely to dislodge);

improved resistance to fragmentation or cracking when manipulated with powered orthopedic tools (saw, drill, burr, reamer); improved ability to create waterproof seals; and improved control of drug delivery rates.

Kits of the Present Disclosure

The present disclosure provides kits comprising two or more of the reactive compositions described herein.

Accordingly, the present disclosure provides a kit comprising Reactive Composition A and Reactive Composition B.

The present disclosure also provides a kit comprising Reactive Composition A and Reactive Composition C.

The present disclosure also provides a kit comprising Reactive Composition D and Reactive Composition E.

The present disclosure also provides a kit comprising Reactive Composition F and Reactive Composition G.

The present disclosure also provides a kit comprising Reactive Composition H and Reactive Composition I.

The present disclosure also provides a kit comprising Reactive Composition J and Reactive Composition K.

The present disclosure also provides a kit comprising Reactive Composition A and Reactive Composition L.

The present disclosure also provides a kit comprising Reactive Composition A and Reactive Composition M.

The present disclosure also provides a kit comprising Reactive Composition A and Reactive Composition N.

The present disclosure also provides a kit comprising Reactive Composition A and Reactive Composition O.

In some aspects, a kit of the present disclosure is provided in a single package. A single package can comprise one or more amounts of any single reactive composition. Thus, in a non-limiting example, a kit of the present disclosure can comprise a package comprising one amount of Reactive Composition A and one amount of Reactive Composition B. In another non-limiting example, a kit of the present disclosure can comprise a package comprising two amounts of Reactive Composition A and two amounts of Reactive Composition B. The two or more reactive compositions can be present in equal amount or unequal amounts.

In some aspects, the packages of the kits of the present disclosure are adapted to permit the removal of one component at a time while leaving the remaining components in a sealed, sterile, environment.

In some aspects, the packages of the kits of the present disclosure are adapted to permit the removal of one set of components at a time while leaving the remaining sets of components in a sealed, sterile, environment. Accordingly, in a non-limiting example, a package of the kits of the present disclosure may comprise two amounts of Reactive Composition A and two amounts of Reactive Composition B for a total of four components. These four components are split into two sets of components (a first set and a second set), each set comprising one amount of Reactive Composition A and one amount of Reactive Composition B. In this non-limiting example, the package can be adapted to allow for the removal of the first set while leaving the second set in a sealed, sterile environment.

In some aspects, a package of the kits of the present disclosure comprises 2 to 12 sets (i.e., 2, 3, 4, 5, 6, 7, 8, 9, 10, 11, or 12 sets) of components, wherein each set comprises two reactive compositions that are to be mixed together.

In some aspects, the package of the kits of the present disclosure comprise an upper peelable film configured to allow the exposure of one set of components (e.g. two reactive compositions that are to be mixed together) at a time.

In some aspects, each component is physically separated from the other components of its set within the package by means of a compartment or plurality of compartments in the package. In some aspects, each set of components may optionally be separated from other sets of the package by perforations allowing the set to be separated either before or after opening and removing the contents.

In some aspects, the plurality of compartments comprises depressions or wells in a heat-sealable metal foil-based sheet. In some aspects, the compartments of a set are flexible and separated by at least one breakable seal adapted to allow the components of the set (e.g. two reactive compositions) to be mixed together when the seal is broken.

In some aspects, the compartments are in the form of one or more syringes, preferably one or more foil-enclosed syringes. In some aspects, the compartments are in the form of a single syringe, preferably a foil-enclosed syringe, adapted to maintain individual components (e.g. individual reactive compositions) of a set separated from each other within the single syringe. In some aspects, the compartments are in the form of a plurality of syringes and each syringe contains a single component of a set.

In some aspects, the package comprises a surface which is in contact with the components, said surface having a surface energy substantially equal to or less than the surface energy of the components, or both, such that the component does not adhere or adheres weakly to the surface. In some aspects, the surfaces of the package that are in contact with the components are coated with a surface having a surface energy substantially equal to or less than the surface energy of the components such that they do not adhere, or adhere weakly to, the surface.

In some aspects, the compartment comprises one or more surfaces in contact with an individual component, the one or more surfaces comprising or consisting of a low surface energy material selected, for example, from the group consisting of polytetrafluoroethylene (PTFE), silicone, polypropylene, polyethylene, and polystyrene.

In some aspects, the kits of the present disclosure are sterile. In some aspects, any individual component of a kit of the present disclosure is sterile.

In some aspects, a package can comprise an outer, heat sealable, preferably water impermeable or water resistant, envelope completely surrounding the package, and a desiccant. In some aspects, the outer envelope is a heat sealed, water impermeable or water resistant foil package.

The kits of the present disclosure can further comprise one or more devices having a pliable structure with an application surface having a surface energy substantially equal to or less than the surface energy of a composition of the present disclosure such that said composition does not adhere or adheres very weakly to the device. The device can be in the form of a sheet. Suitable materials for forming the application surface include, for example, polytetrafluoroethylene (PTFE), silicone, polypropylene, polyethylene, and polystyrene. Such devices are described in US 2012/0035610, which is herein incorporated by reference.

In some aspects, a package has a shelf life of at least 1-2 years. In some aspects, the package has a shelf life of 6 months, 12 months, 18 months, 24 months, or 36 months. Methods of Using the Compositions of the Present Disclosure The present disclosure provides methods wherein two or more reactive compositions are mixed to relative homogeneity by hand or with a mixing apparatus (e.g. with a mortar and pestle) to produce the compositions as described herein (e.g. Composition A+B, Composition A+C, Composition D+E, Composition F+G, Composition H+I, Composition J+K, Composition A+L, Composition A+M, Composition A+N and Composition A+O; hereafter referred to as "final product compositions"). Depending upon the specific reactive compositions that are mixed together, the final product composition will begin to harden over time.

During the hardening phase, the final product compositions may be used in any one of the methods described herein. These methods include, but are not limited to: a) applying the final product compositions to bleeding bone to act as a hemostatic tamponade; b) applying the final product compositions as an adhesive (e.g., to stabilize a bone fracture or re-approximate a sternotomy); c) applying the final product compositions as a bone void filler or cement to fill gaps in the skeletal system, resulting in skeletal fusion, or aid in the adhesion between bone segments, fragments, and/or metallic hardware; and d) custom shaping the final product compositions to create form-fitting fixation devices such as sheets, rods, wraps, or other support structures that can be anchored by plates, sutures, or screws. That is, the composition described herein can be used for orthopedic applications as a bone hemostat, bone adhesive, bone void filler, or a bone cement or a combination thereof.

The use of the term "fully cured", "fully set", "solid", or "hardened" form of the composition of the present disclosure is meant to distinguish this cured, set, solid, or hardened form from the viscous fluid, paste or putty form of the constituent materials/components/putties/pastes that harden upon mixing or kneading. In some aspects, the solid form of the compositions of the present disclosure bond to bone or metal surfaces, and reaches self-supporting bond strength within approximately 90 minutes. In some aspects, the solid form of the compositions of the present disclosure possesses tensile and shear strength equal to natural bone within 72 hours of mixing the constituent materials. In some aspects, the compositions of the present invention formed by mixing or kneading the constituent materials/components/putties harden into a solid form at room temperature or at body temperature in between 5 to 90 minutes.

The term "fluid form" of the compositions as used throughout herein, is a putty, paste or viscous fluid that hardens (i.e., "cures" or "sets") into the final solid form. The fluid form of the compositions of the present disclosure, is moldable or pliable and does not adhere appreciably to surgical gloves or instruments, but adheres well to moist bone surfaces. The fluid form of the compositions of the present disclosure, is resistant to dislodgement by surgical irrigation at the application site. The fluid form of the compositions of the present disclosure, is useful, for example, to fill a cavity in the bone, for injection through a syringe to the site of application, or for bone reconstruction. The fluid form of the compositions of the present disclosure remains in a moldable state at room temperature for up to 120 minutes. In some aspects, the moldability time period of the compositions of the present disclosure varies from 5 to 120 minutes.

Additionally, the present disclosure provides intraoperative use of the compositions of the present disclosure for tissue repair and/or reconstruction. The compositions of the present disclosure can be used for repair and/or reconstitution of two or more pieces of bone, two or more pieces of cartilage, and/or two or more pieces of bone and cartilage.

In the methods described herein, the step of mixing and/or kneading two or more reactive compositions of the present disclosure can comprise mixing and/or kneading Reactive Composition A and Reactive Composition B. In some aspects, the mixing and/or kneading of Reactive Composition A and Reactive Composition B yields the final product composition "Composition A+B".

In the methods described herein, the step of mixing and/or kneading two or more reactive compositions of the present disclosure can comprise mixing and/or kneading Reactive Composition A and Reactive Composition C. In some aspects, the mixing and/or kneading of Reactive Composition A and Reactive Composition C yields the final product composition "Composition A+C".

In the methods described herein, the step of mixing and/or kneading two or more reactive compositions of the present disclosure can comprise mixing and/or kneading Reactive Composition D and Reactive Composition E. In some aspects, the mixing and/or kneading of Reactive Composition D and Reactive Composition E yields the final product composition "Composition D+E".

In the methods described herein, the step of mixing and/or kneading two or more reactive compositions of the present disclosure can comprise mixing and/or kneading Reactive Composition F and Reactive Composition G. In some aspects, the mixing and/or kneading of Reactive Composition F and Reactive Composition G yields the final product composition "Composition F+G".

In the methods described herein, the step of mixing and/or kneading two or more reactive compositions of the present disclosure can comprise mixing and/or kneading Reactive Composition H and Reactive Composition I. In some aspects, the mixing and/or kneading of Reactive Composition H and Reactive Composition I yields the final product composition "Composition H+I".

In the methods described herein, the step of mixing and/or kneading two or more reactive compositions of the present disclosure can comprise mixing and/or kneading Reactive Composition J and Reactive Composition K. In some aspects, the mixing and/or kneading of Reactive Composition J and Reactive Composition K yields the final product composition "Composition J+K".

In the methods described herein, the step of mixing and/or kneading two or more reactive compositions of the present disclosure can comprise mixing and/or kneading Reactive Composition A and Reactive Composition L. In some aspects, the mixing and/or kneading of Reactive Composition A and Reactive Composition L yields the final product composition "Composition A+L".

In the methods described herein, the step of mixing and/or kneading two or more reactive compositions of the present disclosure can comprise mixing and/or kneading Reactive Composition A and Reactive Composition M. In some aspects, the mixing and/or kneading of Reactive Composition A and Reactive Composition M yields the final product composition "Composition A+M".

In the methods described herein, the step of mixing and/or kneading two or more reactive compositions of the present disclosure can comprise mixing and/or kneading Reactive Composition A and Reactive Composition N. In some aspects, the mixing and/or kneading of Reactive Composition A and Reactive Composition N yields the final product composition "Composition A+N".

In the methods described herein, the step of mixing and/or kneading two or more reactive compositions of the present disclosure can comprise mixing and/or kneading Reactive Composition A and Reactive Composition O. In some aspects, the mixing and/or kneading of Reactive Composition A and Reactive Composition O yields the final product composition "Composition A+O".

The present disclosure provides a method of stabilizing, repairing, and/or reapproximating a bone fracture or a sternotomy, the method comprising the steps of: a) mixing together a set of two or more reactive compositions of the present disclosure, to form a final product composition; and b) applying the final product composition to the surfaces of the bone fracture or the cut surfaces of the sternotomy; and c) manually reducing or reapproximating the bone fragments. The methods can further comprise: d) allowing the final product composition to harden into its fully cured, solid form.

In some aspects of the method of stabilizing, repairing, or reapproximating a bone fracture or a sternotomy disclosed herein, step (b) further comprises applying a portion of the final product composition across the surface of a surgical hardware to create a final product composition-hardware construct, and affixing the final product composition-hardware construct to the surfaces of the bone fracture or the cut surfaces of the sternotomy.

In some aspects of the methods of the present disclosure, the mixing or kneading together of two or more reactive compositions of the present disclosure is done by any one of hand mixing or kneading or by using a mixing or kneading apparatus. In some aspects of the methods of the present disclosure, the mixing of the of two or more reactive compositions is accomplished using a dispenser that initially holds the two or more reactive compositions separate from one another, but during dispensation, mixes the two or more reactive compositions together. In a non-limiting example, this dispenser can be a syringe.

In some aspects, the methods for stabilizing, repairing, or reapproximating of bone fragments of the present disclosure comprise mixing or kneading together a set of at least two reactive compositions of the present disclosure to form a final product composition disclosed herein; b) applying a first portion of the composition to the cut or fractured surface of at least one of the pieces of bone; and c) maintaining the pieces of cut or fractured bone in proximity to form a reduced fracture. In some aspects, the pieces of cut or fractured bone are maintained in proximity until the final product composition has hardened and the reduced fracture remains fixed.

In some aspects, the first portion of the final product composition is applied to the cut or fractured surface of at least one of the pieces of bone, either in multiple portions at a plurality of locations of the cut or fractured surface, and interrupted by gaps, or as a single portion across substantially the entire length of the cut or fractured surface. In aspects, the method further comprises compressing the pieces of cut or fractured bone together until the first portion of the final product composition has hardened. In some aspects, the pieces of cut or fractured bone are maintained in proximity for about 2 to 5 minutes. In some aspects, the methods further comprise applying a second portion of the final product composition disclosed herein across the reduced fracture line in the form of a plate or tape. In some aspects, the methods further comprise pressing additional portions of the final product composition into each of two or more drill holes located opposite each other across the reduced fracture line, thereby substantially filling each drill hole. In some aspects, the methods further comprise shaping an additional portion of the final product composition into a rod and joining each end of the rod to a portion of final product composition pressed into a drill hole. In some aspects, the methods further comprise drilling a hole into the final product composition which is in the form of a plate or tape after the final product composition has hardened.

In some aspects of the methods for stabilizing, repairing, or reapproximating of bone fragments of the present disclosure, the bone is a long bone, a short bone, a flat bone, an irregular bone, or a sesamoid bone. In aspects wherein the bone is any one of a long bone or a short bone, the methods further comprise stretching an additional portion of the final product composition into the form of a ribbon or cuff and wrapping the final product composition ribbon or cuff around the circumference of the reduced fracture line. In aspects wherein the bone is a flat bone, the flat bone can be selected from a sternum, rib, scapula, pelvic bone or cranial bone. In aspects wherein the bone is flat bone, the flat bone can be selected from a rib, scapula, or cranial bone. In aspects, wherein the bone is a rib bone, the methods further comprise applying an additional portion of the final product composition into the hollow of the rib bone.

In some aspects, the bone is an irregular bone. In some aspects, the irregular bone is a vertebra. In aspects wherein the bone is a vertebra, the methods further comprise inserting an additional portion of the final product composition into an intervertebral space to form a spacer or cage. In some aspects, the methods further comprise applying a second portion of the final product composition to two or more spinal pedicles adjacent to the final product composition spacer or cage to form two or more final product composition anchor points on the pedicles and either stretching a further portion of final product composition between the anchor points or positioning a rod between the anchor points and pressing the rod into the anchor points, thereby connecting the anchor points.

In some aspects, the methods of the present disclosure can be used to join shattered pieces of bone. In some aspects, the methods for stabilizing, repairing or reapproximating of bone fragments of the present disclosure comprise joining at least two pieces (e.g., 2, 3, 4, 5, 6, 7, 8, 9, or more) of fractured long or short bone. In some aspects, the methods comprise: a) mixing together two or more reactive compositions to form a final product composition; b) dividing the final product composition into at least two portions; c) applying a first portion of the final product composition to the cut or fractured surface of at least one of the pieces of bone; and d) maintaining the at least two pieces of cut or fractured bone in proximity to form a reduced fraction until the final product composition has hardened sufficiently to maintain the reduced fracture repair fixed. The methods can further comprise shaping a second portion of final product composition into the form of a ribbon or cuff and wrapping the final product composition ribbon or cuff around the circumference of the reduced fracture line. The methods can further comprise mixing two or more additional reactive compositions to form one or more additional final product composition(s) and using the one or more additional final product composition(s) in one or more of the following further optional step(s): shaping the one or more additional final product composition(s) into one or more additional ribbon(s) or cuff(s) and wrapping the one or more additional ribbon(s) or cuff(s) around the circumference of the reduced fracture line; pressing portions of the one or more additional final product composition(s) into each of two or more drill holes located opposite each other across the reduced fracture line, thereby substantially filling each drill hole; and/or shaping a portion of the one or more additional final product composition(s) into a rod and joining each end of the rod to a portion of final product composition pressed into a drill hole (e.g., by bending each end of the rod in order to fit it into a drill hole).

In some aspects, the methods for stabilizing, repairing, or reapproximating of bone fragments of the present disclosure comprises: a) mixing two or more reactive compositions to form a final product composition; b) forming the final product composition into the form of a ribbon or cuff; and c) wrapping the final product composition ribbon or cuff around a circumference of the reapproximated long or short bone, thereby applying an internal orthopedic cast to a reapproximated long or short bone.

In some aspects of the methods for stabilizing, repairing or reapproximating of bone fragments of the present disclosure, the bone fracture is of one or more vertebra (e). In some aspects, the methods comprise: a) mixing two or more reactive compositions to form a final product composition; and b) inserting a first portion of the final product composition into an intervertebral space to form a spacer or cage. The methods can optionally comprise dividing the final product composition into two or more portions. In some aspects, the methods further comprise introducing one or more of an autograft material, an allograft material, and/or a bone substitute material into one or more hole(s) drilled into the final product composition spacer or cage. In some aspects, the methods further comprise applying a second portion of the final product composition to two or more spinal pedicles adjacent to the final product composition spacer or cage to form two or more of the final product composition anchor points on the pedicles and either stretching a further portion of the final product composition between the anchor points or positioning a rod between the anchor points and pressing the rod into the anchor points, thereby connecting the anchor points.

In some aspects, the methods for stabilizing, repairing, or reapproximating of bone fragments of the present disclosure comprise: a) mixing two or more reactive compositions to form a final product composition of the present disclosure; b) applying a first portion of the final product composition to one or more surfaces of a bone fragment and/or to the surface of a bone void to be filled by the fragment; and c) pressing the fragment into the void.

In some aspects, the methods for stabilizing, repairing, or reapproximating of bone fragments of the present disclosure comprise: a) mixing two or more reactive compositions to form a final product composition; b) applying a first portion of the final product composition to one or more surface(s) of a bone fragment and/or to the surface of a bone void to be filled by the fragment; and c) pressing the fragment into the void. In some aspects, the methods further comprise applying a second portion of the final product composition across the reapproximated surface in the form of a plate or tape. In some aspects, the methods further comprise pressing additional portions of the final product composition into each of two or more drill holes located adjacent to each other, or opposite each other across the fracture line, thereby substantially filling each drill hole.

In some aspects, the methods for stabilizing, repairing, or reapproximating of bone fragments of the present disclosure further comprise stabilizing a surgical screw as part of the stabilization, repair, or reapproximation of a bone fracture. The methods can comprise: a) mixing two or more reactive compositions to form a final product composition; b) filling a drilled or tapped hole with a portion of the final product composition; and c) inserting the screw into the final product composition before it hardens. Alternatively, step (c) can comprise setting the screw into the final product composition after it hardens.

The present disclosure provides methods for repair of cartilaginous tissue using the compositions described herein. The methods comprise: a) mixing two or more reactive compositions to form a final product composition; and b) applying the final product composition into a void or space formerly occupied by cartilaginous tissue in an amount sufficient to substantially fill the void or space.

In some aspects, the methods for stabilizing, repairing, or reapproximating of bone fragments of the present disclosure can further comprise stabilizing one or more pieces of surgical hardware as part of the stabilization, repair, or reapproximation of a bone fracture. The methods can comprise: a) mixing two or more reactive compositions to form a final product composition; and b) applying a portion of the final product composition between the surface of a bone and the surgical hardware and/or by applying a portion of the final product composition across the surface of the surgical hardware after it has been affixed to the bone. In some aspects, the methods comprise: a) mixing two or more reactive compositions to form a final product composition; b) combining the final product composition with the surgical hardware and/or by applying a portion of the final product composition across the surface of the surgical hardware to form a final product composition-hardware construct; and c) affixing the final product composition-hardware construct to the bone. In some aspects, the surgical hardware is a plate, a screw, a mesh, a nail, a cap, a wire, a flap, or a similar surgical device known in the art, or any combination thereof. In some aspects, the screw is a fenestrated screw that comprises a canula or cavity along the shaft or body of the screw. In some aspects, the methods comprise applying a portion of final product composition through the canula or cavity of the screw.

The present disclosure provides methods of stabilizing surgical hardware for stabilizing, repairing, or reapproximating a bone fracture, the method comprising the steps of: a) intraoperatively mixing or kneading together two or more reactive compositions to form a final product composition; b) combining the final product composition with the surgical hardware, and/or applying the mixed or kneaded final product composition to the surfaces of the bone fracture or the cut surfaces of the sternotomy; and c) manually reducing the bone fragments while allowing the final product composition to set.

In some aspects of the methods of stabilizing a surgical hardware disclosed herein, the surgical hardware is any one of a plate, a screw, a mesh, a nail, a cap, a wire, a flap or a combination thereof. In some aspects of the methods of stabilizing a surgical hardware, the bone fracture is any one of a cranial bone fracture or defect, a pelvic bone fracture or defect or long bone fracture. In some aspects of the methods of stabilizing a surgical hardware, the methods further comprise applying the mixed or kneaded final product composition to the surfaces of the bone fracture or the cut surfaces of the sternotomy through a surgical mesh to create a cap or a flap, and reducing or reapproximating the bone fragments while allowing the final product composition to set; and allowing the composition to harden into its fully cured solid form. In some aspects of the methods of stabilizing a surgical hardware, the methods further comprise customizing the plate or flap by cutting or otherwise machining the mesh prior to or after the final product composition is applied to the mesh or flap.

In some aspects, the final product compositions of the present disclosure has mechanical properties suitable for drilling and/or accepting a surgical screw without shattering or splintering. In some aspects, the final product compositions provided herein can be used in combination with a surgical hardware, e.g., a screw, a plate, a wire, a rod, or a nail, wherein the composition is used as an adhesive to keep the surgical hardware in contact with a bone. In some aspects, the final product compositions provided herein can be used in combination with a surgical hardware, e.g. a screw, a plate, a wire, a rod, or a nail, wherein the final product composition is used as a material to drill, affix, or insert the surgical hardware. In some aspects, the surgical hardware can be a cannulated surgical hardware, wherein the cannulation of the surgical hardware comprises one or more of the compositions disclosed herein. In some aspects, the cannulated surgical hardware can comprise at least one fenestration to allow the compositions to extrude from the cannulation of the surgical hardware into the surrounding bone.

Accordingly, the present disclosure also provides cannulated bone screws having a shaft, a tip, and a head, with at least a portion of said shaft having threads thereon configured to be inserted into a bone, wherein the screw comprises a cannulation along the shaft comprising an amount of one or more compositions disclosed herein within the cannulation, and at least one fenestration disposed along the shaft of the screw and connected to the cannulation of the screw, wherein the fenestration allows the composition to pass through the at least one fenestration of the screw into a bone.

In some aspects, the cannulated bone screw can be configured for insertion into a hole drilled in a bone. In some aspects, the cannulated bone screw can be configured for securing in the hole drilled in a bone by an amount of the composition disclosed herein that is in contact with the outer surface of the screw and the walls of the hole. In some aspects, the cannulated bone screw can be configured for securing into a bone by a surgical plate. In some aspects, the cannulated bone screw can be configured for securing into a bone by at least one surgical nail. In some aspects, the cannulated bone screw can be configured for securing to the bone by a nut or a washer.

In some aspects, the cannulated bone screw can be for use in fracture line reduction between two or more pieces of a bone. In some aspects, the site of the bone can be a surgical site or a site of injury.

In some aspects, the bone screw can be for use in a method of stabilizing, repairing, or reapproximating a bone fracture or a sternotomy, disclosed herein. In some aspects, the method of stabilizing, repairing or reapproximating a bone fracture can be a method of bone surgery of the bone of a jaw, hip, pelvis, knee, ankle, and foot. In some aspects, the method of bone surgery can be a surgery of phalanx, metacarpals, radius, ulna, fibula, femur, clavicle, humerus, tibia, scapula, vertebra, pelvis, or rib. In some aspects, the method of bone surgery can be arthroscopy, joint replacement, revision joint surgery, bone fracture repair, debridement, fusion of bones, spine fusion, or osteotomy. In some aspects, the method of bone surgery can be ankle fracture repair, knee arthroscopy, knee replacement, repair of femoral neck fracture and trochanteric fracture, hip replacement, wrist bone (distal radius) fracture repair, shoulder arthroscopy, laminectomy, lumbar spinal fusion, lower back intervertebral disc surgery, forearm (radius and/or ulna) bone fracture repair, thigh bone (femoral shaft) fracture repair, or an orthodontic surgery.

In some aspects, the cannulated bone screw can be used for any of the following: joining two pieces of a fractured bone, securing a surgical hardware (e.g., a plate, a rod or a cap or a replacement thereof to a bone), and/or maintaining or positioning one or more bones in a desired anatomical position or orientation.

In some aspects, the cannulated bone screw can be a cortical screw, a cancellous screw or a Herbert screw. In some aspects, the cannulated bone screw can be a dynamic hip screw, Acutrak screw, malleolar screw, a locking bolt screw, an interference screw, or a pedicle. In some aspects, the cannulated bone screw can further comprise a central opening in the outer end of the head of the screw configured for receiving a driving tool for driving the screw into the bone, and for receiving the composition of the present disclosure.

In some aspects, the cannulated bone screw can be inserted into a bone of a hip, pelvis, knee, ankle, and/or foot. In some aspects, the cannulated bone screw can be inserted into a bone or portion of phalanx, metacarpals, radius, ulna, fibula, femur, clavicle, humerus, tibia, scapula, vertebra, pelvis, or rib.

Accordingly, the present disclosure provides methods of delivering one or more compositions of the present disclosure into a site in a bone of a patient in need thereof, the method comprising: a) providing one of more of the cannulated bone screw disclosed herein; b) inserting the cannulated bone screw into the bone of the patient; and c) allowing the amount of the composition within the bone screw to be delivered into the bone.

In some aspects, the step of providing the cannulated bone screw disclosed herein further comprises delivering an amount of the composition disclosed herein, into the cannulation of the bone screw. In some aspects, the delivering of an amount of the composition into the cannulation can be done by means of a syringe, wherein the syringe is connected to the central opening in the outer end of the head of the screw. In some aspects, the delivering of an amount of a composition into the cannulation of the cannulated bone screw can be done from a reservoir that is connected to the central opening in the outer end of the head of the screw by means of a pump.

In some aspects, the inserting of a cannulated bone screw into the bone of the patient can be done by drilling the screw into the bone. In some aspects, inserting the cannulated bone screw into the bone of the patient can be done by: a) drilling a hole in the bone of the patient; b) filling the hole with one or more of the compositions disclosed herein; c) allowing the composition in the drilled hole of the bone to solidify; and d) inserting the screw disclosed herein through the solidified final product composition in the drilled hole of the bone.

In some aspects, the compositions of the present disclosure can be for use in a method of securing surgical hardware into a bone of a subject in need thereof, wherein the surgical hardware has a body and an opening at a point of the body, wherein the surgical hardware is cannulated inside the body of the hardware, and comprises at least one fenestration along the body of the hardware for receiving a composition of the present disclosure, wherein the methods comprise: a) inserting the surgical hardware into a site on the bone; b) delivering the composition inside through the opening into the cannulation in the body of the surgical hardware; c) allowing the composition to pass through the fenestration of the surgical hardware into an area surrounding the hardware in the bone; and d) allowing the composition to harden to secure the surgical hardware to the bone. In some aspects, the surgical hardware can be a screw, a plate, a wire, a rod, a nail, or equivalent thereof.

In some aspects, the compositions of the present disclosure can be for use in methods for stabilizing, repairing, or reapproximating of bone fragments of the present disclosure, wherein the methods comprise: a) mixing or kneading together two or more reactive compositions to form a final product composition; b) applying the final product composition to the surfaces of the bone fracture or the cut surfaces of the sternotomy through a surgical mesh to create a cap or a flap; and c) manually reducing or reapproximating the bone fragments while allowing the composition to set. In some aspects, the method further comprises customizing the plate or flap by cutting or otherwise machining the mesh prior to or after the final product composition is applied to the mesh or flap.

The methods of the present disclosure can optionally comprise dividing the final product composition into two or more portions.

The compositions of the present disclosure can also be used in methods for sealing voids and gaps in one or more bones in a subject following the implantation of a radiation therapy device in the subject. Without wishing to be bound by theory, the compositions of the present disclosure inhibit and/or modulate the leakage of radiation from inside the subject. Such inhibition and/or modulation is advantageous for several different reasons, including, but not limited to: preventing undesirable radiation exposure within the subject beyond the targeted area; preventing radiation exposure of other persons and the environment surrounding the subject; and increasing the effectiveness of the radiation therapy by limiting leakage of radiation away from the target area.

As would be appreciated by the skilled artisan, implantable radiation therapy devices can be used for the treatment of brain cancer. In such methods, clinicians implant the radiation therapy device in the brain cavity via a cranial flap that is opened in the skull. Accordingly, in one non-limiting example, these compositions of the present disclosure can be used to seal a cranial flap following implantation of a radiation therapy device into the brain cavity for the treatment of brain cancer. Without wishing to be bound by theory, without the use of the compositions of the present invention to seal the cranial flap, radiation would be able to freely escape out of the brain cavity, decreasing both the effectiveness of the radiation therapy device as well as its safety (due to off-target radiation effects).

As would be appreciated by the skilled artisan, examples of radiation therapy devices that can be implanted within a subject include, but are not limited to, GammaTile® (a collagen tile comprising four ceisum-131 (Cs-131) radiation emitting seeds; see Gessler D J, Ferreira C, Dusenbery K, Chen C C. Future Oncol. 2020 October; 16 (30): 2445-2455. doi: 10.2217/fon-2020-0558. PMID: 32618209), BRACHY-SOURCE® Seed Implants, and GliaSite RTS. Radiation therapy devices that can be implanted within a subject include any device for radionuclide brachytherapy that is known in the art.

Accordingly, the present disclosure provides a method for treating a brain cancer, the method comprising: a) implanting a radiation therapy device in a subject via a cranial flap; b) mixing or kneading together two or more reactive compositions of the present disclosure to form a final product composition of the present disclosure; c) sealing the cranial flap using the final product composition.

In some aspects, the brain cancer can be selected from a group comprising Acoustic Neuroma, Pilocytic Astrocytoma, Low-grade Astrocytoma, Anaplastic Astrocytoma, Glioblastoma multiforme (GBM), Chordoma, CNS Lymphoma, Craniopharyngioma, Brain Stem Glioma, Ependymoma, Mixed Glioma, Optic Nerve Glioma, Subependymoma, Medulloblastoma, Meningioma, Metastatic Brain Tumors, Oligodendroglioma, Pituitary Tumors, Primitive Neuroectodermal (PNET), Schwannoma, Brain Stem Glioma, Craniopharyngioma, Ependymoma, Juvenile Pilocytic Astrocytoma (JPA), Medulloblastoma, Optic Nerve Glioma, Pineal Tumor, Primitive Neuroectodermal Tumors (PNET), or Rhabdoid Tumor. The brain cancer can be Glioblastoma multiforme.

General Definitions

As used herein, the terms "patient" or "subject" are used interchangeably herein to refer to any mammal, including humans, domestic and farm animals, and zoo, sports, and pet animals, such as dogs, horses, cats, and agricultural use animals including cattle, sheep, pigs, and goats. One preferred mammal is a human, including adults, children, and the elderly. A subject may also be a pet animal, including dogs, cats, and horses. Preferred agricultural animals would be pigs, cattle, and goats.

The phrases "therapeutically effective amount" and "effective amount" and the like, as used herein, indicate an amount necessary to administer to a patient, or to a cell, tissue, or organ of a patient, to achieve a therapeutic effect, such as an ameliorating or, alternatively, a curative effect. The effective amount is sufficient to elicit the biological or medical response of a cell, tissue, system, animal, or human that is being sought by a researcher, veterinarian, medical doctor, or clinician. Determination of the appropriate effective amount or therapeutically effective amount is within the routine level of skill in the art.

The term "putty" and the likes refer to soft, moldable, cohesive compositions, as used herein refers to most often formed viscous suspensions or viscoelastic composites (i.e., dispersions of particles in a viscous fluid). The terms putty and paste are qualitative and generally describe a composition that is moldable/formable and flowable, respectively.

The terms "absorbable", "degradable", "biodegradable", "resorbable", and the like are used interchangeably herein to refer to the ability of the claimed compositions to degrade (partially or completely) under physiological conditions into non-toxic products that can be metabolized or excreted from the body within a period of time, generally several days and up to a year or about 18 to 24 months (i.e., 18, 19, 20, 21, 22, 23, or 24 months) or longer. In some aspects, the composition is fully biodegradable within about 12 months.

The terms "nonabsorbable", "non-degradable", "non-biodegradable", "non-resorbable", and the like are used interchangeably herein to refer to the inability of the compositions to degrade (partially or completely) under physiological conditions.

EXPERIMENTAL EXAMPLES

Example 1

In this non-limiting example, a first reactive composition and a second reactive composition were hand mixed to homogeneity to form a final product composition. Final Product compositions that were tested include:

Final Product Composition A+L, formed by the mixing of Reactive Composition A and Reactive Composition L, and referred to by "Gentamycin" in FIG. 1.

Final Product Composition A+M, formed by the mixing of Reactive Composition A and Reactive Composition M, referred to by "Tobramycin" in FIG. 1

Final Product Composition A+N, formed by the mixing of Reactive Composition A and Reactive Composition N, referred to by "Vancomycin" In FIG. 1

Immediately following mixing, the final product compositions were formed into spheres and placed into specimen jars containing pH 7.4 phosphate buffer saline at 37° Celsius (C), with a ratio of putty sample to elution buffer of 1:10. Samples were incubated at 37° C. and samples taken at defined timepoints for analysis by HPLC or spectrophotometric, as appropriate, to quantify antibiotic elution. The elution buffer was exchanged daily with fresh phosphate buffer to maintain sink conditions for elution. The results of this analysis are shown in FIG. 1

Example 2

In this non-limiting example, a first reactive composition and a second reactive composition were hand mixed to homogeneity to form a final product composition. Final Product compositions that were tested include:

Final Product Composition A+M, formed by the mixing of Reactive Composition A and Reactive Composition M, referred to by "Tobramycin loaded" in Tables 1-3.

Final Product Composition A+N, formed by the mixing of Reactive Composition A and Reactive Composition N, referred to by "Vancomycin loaded" in Tables The Final Product Compositions were placed inside a container that was inoculated with a different test strains of bacteria, including *S. aureus* ATCC 29213 (Table 1), *P. aeruginosa* ATCC 27853 (Table 2), *E. cloacae* CDC 0073 (Table 3). The ratio of Final Product Composition to media was approximately 1:5 (see Stravinskas et al. Bone Joint Res. 2016 September; 5 (9): 427-35. doi: 10.1302/2046-3758.59.BJR-2016-0108.R1), while media without the Final Product Composition was used as growth control. Bacteria recovery was assessed at the following time points: 0, 4, and 24 hours. At each time point a portion of the media was removed and 10-fold serially diluted. Dilutions were plated in duplicates for CFU enumeration. The results are shown in Tables 1-3.

TABLE 1

| *S. aureus* ATCC 29213 | Average CFU/mL | | |
|---|---|---|---|
| Test condition | Inoculum (Time 0) | 4 hours | 24 hours |
| Control (no antibiotic) | 9.4E+06 | 1.0E+09 | 1.3E+09 |
| Vancomycin loaded | | 3.4E+05 | 1.0E+01 |
| Tobramycin loaded | | 1.0E+01 | 1.0E+01 |

TABLE 2

| *P. aeruginosa* ATCC 27853 | Average CFU/mL | | |
|---|---|---|---|
| Test condition | Inoculum (Time 0) | 4 hours | 24 hours |
| Control (no antibiotic) | 2.1E+06 | 3.2E+07 | 6.9E+08 |
| Vancomycin loaded | | 5.2E+07 | 4.7E+08 |
| Tobramycin loaded | | 1.0E+01 | 1.0E+01 |

TABLE 3

| *E. cloacae* CDC 0073 | Average CFU/ml | | |
|---|---|---|---|
| Test condition | Inoculum (Time 0) | 4 hours | 24 hours |
| Control (no antibiotic) | 2.1E+06 | 3.1E+08 | 1.3E+09 |
| Vancomycin loaded | | 1.4E+08 | 8.9E+07 |
| Tobramycin loaded | | 1.0E+01 | 1.0E+01 |

Example 3

In this non-limiting example, the below characteristics were individually determined for compositions comprising Reactive Composition A or Reactive Composition F.

Compositions comprising Composition A or Reactive Composition F demonstrate a minimum shelf stability of 36 months. In addition, compositions comprising Composition A or Reactive Composition F demonstrated mixability (i.e., ability to be easily mixed) to form a homogenous mixture (i.e., appropriate for end-use application to a subject) within 60 seconds.

Compositions comprising Composition A or Reactive Composition F demonstrated desirable manufacturing features. Compositions comprising Composition A or Reactive Composition F demonstrated extrudability during manufacturing using pressures of less than 35 pounds per square inch (psi) and by-hand mixability. In addition, compositions comprising Composition A or Reactive Composition F had a dark color which is desirable for contrast with the use of alternate constituent(s).

Example 4

In this non-limiting example, the below characteristics were individually determined for compositions comprising Reactive Composition B, Reactive Composition C, or Reactive Composition G.

Compositions comprising Reactive Composition B, Reactive Composition C, or Reactive Composition G demonstrate a minimum shelf stability of 36 months. In addition, compositions comprising Reactive Composition B, Reactive Composition C, or Reactive Composition G demonstrated mixability to a homogenous mixture (i.e., appropriate for end-use application to a subject) within about 60 seconds.

Compositions comprising Reactive Composition B, Reactive Composition C, or Reactive Composition G demonstrated desirable manufacturing features. Compositions comprising Reactive Composition B, Reactive Composition C, or Reactive Composition G demonstrated extrudability during manufacturing using pressures of less than 35 pounds per square inch (psi) and by-hand mixability. In addition, compositions comprising Reactive Composition B, Reactive Composition C, or Reactive Composition G had a light color which is desirable for contrast with the use of alternate constituent(s).

Example 5

In this non-limiting example, the below characteristics were individually determined for compositions comprising Reactive Composition D, Reactive Composition H, or Reactive Composition N.

Compositions comprising Reactive Composition D, Reactive Composition H, or Reactive Composition N demonstrate a minimum shelf stability of 12 months. In addition, compositions comprising Reactive Composition D, Reactive Composition H, or Reactive Composition N demonstrated mixability to a homogenous mixture (i.e., appropriate for end-use application to a subject) within 60 seconds.

Compositions comprising Reactive Composition D, Reactive Composition H, or Reactive Composition N demonstrated desirable manufacturing features. Compositions comprising Reactive Composition D, Reactive Composition H, or Reactive Composition N demonstrated extrudability during manufacturing using pressures of less than 35 pounds per square inch (psi) and by-hand mixability. In addition, compositions comprising Reactive Composition D, Reactive Composition H, or Reactive Composition N had a dark color which is desirable for contrast with the use of alternate constituent(s).

Compositions comprising Reactive Composition D, Reactive Composition H, or Reactive Composition N comprised sufficient viscosity for filling a syringe barrel, as observed during manufacturing. Moreover, the viscosity of compositions comprising Reactive Composition D, Reactive Composition H, or Reactive Composition N allowed for dispensing through a cannula with an inner diameter as low as 2 mm and allowed for mixing via static mixing elements.

Example 6

In this non-limiting example, the below characteristics were individually determined for compositions comprising Reactive Composition E, Reactive Composition I, or Reactive Composition O.

Compositions comprising Reactive Composition E, Reactive Composition I, or Reactive Composition O demonstrate a minimum shelf stability of 12 months. In addition, compositions comprising Reactive Composition E, Reactive Composition I, or Reactive Composition O demonstrated mixability to a homogenous mixture (i.e., appropriate for end-use application to a subject) within 60 seconds.

Compositions comprising Reactive Composition E, Reactive Composition I, or Reactive Composition O demonstrated desirable manufacturing features. Compositions comprising Reactive Composition E, Reactive Composition I, or Reactive Composition O demonstrated extrudability during manufacturing using pressures of less than 35 pounds per square inch (psi) and by-hand mixability. In addition, compositions comprising Reactive Composition E, Reactive Composition I, or Reactive Composition O had a light color which is desirable for contrast with the use of alternate constituent(s).

Compositions comprising Reactive Composition E, Reactive Composition I, or Reactive Composition O comprised sufficient viscosity for filling a syringe barrel, as observed during manufacturing. Moreover, the viscosity of compositions comprising Reactive Composition E, Reactive Composition I, or Reactive Composition O allowed for dispensing through a cannula with an inner diameter as low as 2 mm and allowed for mixing via static mixing elements.

Example 7

In this non-limiting example, the below characteristics were individually determined for compositions comprising Reactive Composition J or Reactive Composition L.

Compositions comprising Reactive Composition J or Reactive Composition L demonstrate a minimum shelf stability of 12 months. In addition, compositions comprising Reactive Composition J or Reactive Composition L demonstrated mixability to a homogenous mixture (i.e., appropriate for end-use application to a subject) within 60 seconds.

Compositions comprising Reactive Composition J or Reactive Composition L demonstrated desirable manufacturing features. Compositions comprising Reactive Composition J or Reactive Composition L demonstrated extrudability during manufacturing using pressures of less than 35 pounds per square inch (psi) and by-hand mixability. In addition, compositions comprising Reactive Composition J or Reactive Composition L had a dark color which is desirable for contrast with the use of alternate constituent(s).

Example 8

In this non-limiting example, the below characteristics were individually determined for compositions comprising Reactive Composition K or Reactive Composition M.

Compositions comprising Composition K or Reactive Composition M demonstrate a minimum shelf stability of 12 months. In addition, compositions comprising Composition K or Reactive Composition M demonstrated mixability to a homogenous mixture (i.e., appropriate for end-use application to a subject) within 60 seconds.

Compositions comprising Composition K or Reactive Composition M demonstrated desirable manufacturing features. Compositions comprising Composition K or Reactive Composition M demonstrated extrudability during manufacturing using pressures of less than 35 pounds per square inch (psi) and by-hand mixability. In addition, compositions comprising Composition K or Reactive Composition M had a light color which is desirable for contrast with the use of alternate constituent(s).

Example 9

In this non-limiting example, the below characteristics were individually determined for compositions comprising a mixture of Reactive Composition A and Reactive Composition B (i.e., Composition A+B).

Composition A+B demonstrated about 2 minutes of spreadability, wherein 0.25 cc of material can be applied in a thin layer over a surface of greater than 2 cm. In addition, it was observed that Composition A+B demonstrated 6 additional minutes of moldability to contour exterior surfaces at the application site. Composition A+B had the immediate physical properties to hold bone fragments together and further allow for fragment manipulation for up to about 2 minutes. In addition, Composition A+B demonstrated beneficial physical properties which allowed for the insertion of hardware (e.g., a surgical screw) for up to 2 minutes. After about 2 minutes, a drill is needed to insert the hardware. It was observed that Composition A+B had the ability to be immediately physically manipulated with standard orthopedic tools such as a burr, drill, saw, and reamer. Composition A+B also had the ability to resist irrigation and not disperse in bodily fluids. Lastly, Composition A+B demonstrated a volumetric expansion of no more than 10% upon application.

Example 10

In this non-limiting example, the below characteristics were individually determined for compositions comprising a mixture of Reactive Composition A and Reactive Composition C (i.e., Composition A+C).

Composition A+C demonstrated about 30 seconds of spreadability, wherein 0.25 cc of material can be applied in a thin layer over a surface of greater than 2 cm. In addition, it was observed that Composition A+C demonstrated 4 additional minutes of moldability to contour exterior surfaces at the application site. Composition A+C had the immediate physical properties to hold bone fragments together and further allow for fragment manipulation for up to about 30 seconds. Composition A+C has beneficial physical properties that allowed for the insertion of hardware (e.g., a surgical screw) immediately after application to the treatment surface. It was observed that Composition A+C had the ability to be immediately physically manipulated with standard orthopedic tools such as a burr, drill, saw, and reamer. Composition A+C also had the ability to resist irrigation and not disperse in bodily fluids. Lastly, Composition A+C demonstrated a volumetric expansion of no more than 10% upon application.

Example 11

In this non-limiting example, the below characteristics were individually determined for compositions comprising a mixture of Reactive Composition D and Reactive Composition E (i.e., Composition D+E).

Composition D+E demonstrated about 2 minutes of spreadability, wherein 0.25 cc of material can be applied in a thin layer over a surface of greater than 2 cm. In addition, it was observed that Composition D+E demonstrated 6 additional minutes of moldability to contour exterior surfaces at the application site. Composition D+E has the immediate physical properties to hold bone fragments together and further allow for fragment manipulation for up to about 2 minutes. Composition D+E has beneficial physical properties that allow for the insertion of hardware (e.g., a surgical screw) for up to about 2 minutes after application. It was observed that Composition D+E had the ability to be physically manipulated with standard orthopedic tools such as a burr, drill, saw, and reamer after about 2 minutes of post-application. Composition D+E also had the ability to resist irrigation and not disperse in bodily fluids. Lastly, Composition D+E demonstrated a volumetric expansion of no more than 12% upon application.

Example 12

In this non-limiting example, the below characteristics were individually determined for compositions comprising a mixture of Reactive Composition F and Reactive Composition G (i.e., Composition F+G).

Composition F+G demonstrated about 4 minutes of spreadability, wherein 0.25 cc of material can be applied in a thin layer over a surface of greater than 2 cm. In addition, it was observed that Composition F+G demonstrated 12 additional minutes of moldability to contour exterior surfaces at the application site. Composition F+G has the immediate physical properties to hold bone fragments together and further allow for fragment manipulation for up to about 4 minutes. Composition F+G has beneficial physical properties which allow for the insertion of hardware (e.g., a surgical screw) immediately after application to the treatment surface. It was observed that Composition F+G had the ability to be immediately physically manipulated with standard orthopedic tools such as a burr, drill, saw, and reamer. Composition F+G also had the ability to resist irrigation and not disperse in bodily fluids. Lastly, Composition F+G demonstrated a volumetric expansion of no more than 10% upon application.

Example 13

In this non-limiting example, the below characteristics were individually determined for compositions comprising a mixture of any one of: Reactive Composition H+I, or Reactive Composition A+L, or Reactive Composition A+M, or Reactive Composition A+N, or Reactive Composition A+O.

Each of Reactive Composition H+I, Reactive Composition A+L, Reactive Composition A+M, Reactive Composition A+N, and Reactive Composition A+O demonstrated about 2 minutes of spreadability, wherein 0.25 cc of material can be applied in a thin layer over a surface of greater than 2 cm. In addition, it was observed that each of Reactive Composition H+I, Reactive Composition A+L, Reactive Composition A+M, Reactive Composition A+N, and Reactive Composition A+O demonstrated 6 additional minutes of moldability to contour exterior surfaces at the application site. Each of Reactive Composition H+I, Reactive Composition A+L, Reactive Composition A+M, Reactive Composition A+N, and Reactive Composition A+O had the immediate physical properties to hold bone fragments together and further allow for fragment manipulation for up to about 2 minutes. Each of Reactive Composition H+I, Reactive Composition A+L, Reactive Composition A+M, Reactive Composition A+N, and Reactive Composition A+O have the beneficial physical properties that allowed for the insertion of hardware (e.g., a surgical screw) after 2 minutes after application to the treatment surface. It was observed that each of Reactive Composition H+I, Reactive Composition A+L, Reactive Composition A+M, Reactive Composition A+N, and Reactive Composition A+O had the ability to be physically manipulated with standard orthopedic tools such as a burr, drill, saw, and reamer after 2 minutes post-application. Each of Reactive Composition H+I, Reactive Composition A+L, Reactive Composition A+M, Reactive Composition A+N, and Reactive Composition A+O also had the ability to resist irrigation and not disperse in bodily fluids. Lastly, each of Reactive Composition H+I, Reactive Composition A+L, Reactive Composition A+M, Reactive Composition A+N, and Reactive Composition A+O demonstrated a volumetric expansion of no more than 12% upon application.

Each of Reactive Composition H+I, Reactive Composition A+L, Reactive Composition A+M, Reactive Composition A+N, and Reactive Composition A+O demonstrated a radiopacity greater than calcium phosphate.

Example 14

In this non-limiting example, the below characteristics were individually determined for compositions comprising a mixture of Reactive Composition J and Reactive Composition K (i.e., Composition J+K).

Composition J+K demonstrated about 2 minutes of spreadability, wherein 0.25 cc of material can be applied in a thin layer over a surface of greater than 2 cm. In addition, it was observed that Composition J+K demonstrated 6 additional minutes of moldability to contour exterior surfaces at the application site. Composition J+K had the immediate physical properties to allow to hold bone fragments together and allow for fragment manipulation for up to about 2 minutes. Composition J+K has beneficial physical properties which allow for the insertion of hardware (e.g., a surgical screw) immediately after application to the treatment surface for up to about 2 minutes post application without the need for drilling. It was observed that Composition J+K had the ability to be immediately physically manipulated with standard orthopedic tools such as a burr, drill, saw, and reamer. Composition J+K also had the ability to resist irrigation and not disperse in bodily fluids. Lastly, Composition J+K demonstrated a volumetric expansion of no more than 10% upon application.

Composition J+K demonstrated permanent implantation (i.e., non-absorbable profile) within the body.

Exemplary Embodiments

Embodiment 1. A composition comprising:
about 33.1 wt % to about 35.1. wt % ALD;
about 1.7 wt % to about 3.7 wt % PCL;
about 5.5 wt % to about 7.5 wt % tocopherol acetate;
about 50.7 wt % to about 52.7 wt % HA/β-TCP granules; and
about 3.9 wt % to about 5.9 wt % β-TCP powder,
preferably wherein the composition comprises:
    about 34.1 wt % ALD;
    about 2.7 wt % PCL;
    about 6.5 wt % tocopherol acetate;
    about 51.7 wt % HA/β-TCP granules; and
    about 4.9 wt % β-TCP powder.
Embodiment 2. A composition comprising:
about 5.9 wt % to about 7.9 wt % ALD;
about 4.3 wt % to about 6.3 wt % PCL;
about 0.9 wt % to about 2.9 wt % BDO;
about 2.8 wt % to about 4.8 wt % tocopherol acetate;
about 1.3 wt % to about 3.3 wt % triacetin;
about 0.1 wt % to about 1.6 wt % calcium stearate;
about 18.3 wt % to about 20.3 wt % HA/β-TCP granules; and
about 59 wt % to about 61 wt % β-TCP powder,
preferably wherein the composition comprises:
    about 6.9 wt % ALD;
    about 5.3 wt % PCL;
    about 1.9 wt % BDO;
    about 3.8 wt % tocopherol acetate;
    about 2.3 wt % triacetin;
    about 0.6 wt % calcium stearate;
    about 19.3 wt % HA/β-TCP granules; and
    about 60 wt % β-TCP powder.
Embodiment 3. A composition comprising:
about 4.2 wt % to about 6.2 wt % ALD;
about 3 wt % to about 5 wt % PCL;
about 0.1 wt % to about 2.1 wt % BDO;
about 1.6 wt % to about 3.6 wt % TEA;
about 3.6 wt % to about 5.6 wt % tocopherol acetate;
about 1.2 wt % to about 3.2 wt % triacetin;
about 0.1 wt % to about 1.4 wt % calcium stearate,
about 14.2 wt % to about 16.2 wt % HA/β-TCP granules, and
about 63.7 wt % to about 65.7 wt % β-TCP powder,
preferably wherein the composition comprises:
    about 5.2 wt % ALD;
    about 4 wt % PCL;
    about 1.1 wt % BDO;
    about 2.6 wt % TEA;
    about 4.6 wt % tocopherol acetate;
    about 2.2 wt % triacetin;
    about 0.4 wt % calcium stearate;
    about 15.2 wt % HA/β-TCP granules; and
    about 64.7 wt % β-TCP powder.
Embodiment 4. A composition comprising:
about 38.9 wt % to about 40.9 wt % ALD;
about 6.2 wt % to about 8.2 wt % tocopherol acetate;
about 0.01 wt % to about 1.1 wt % calcium stearate;
about 6.9 wt % to about 8.9 wt % β-TCP powder; and
about 43.8 wt % to about 45.8 wt % HA powder,
preferably wherein the composition comprises:
    about 39.9 wt % ALD;
    about 7.2 wt % tocopherol acetate;

about 0.1 wt % calcium stearate;

about 7.9 wt % β-TCP powder; and about 44.8 wt % HA powder.

Embodiment 5. A composition comprising:

about 0.1 wt % to about 1.9 wt % ALD;

about 27.6 wt % to about 29.6 wt % PCL;

about 0.1 wt % to about 1.9 wt % BDO;

about 6.9 wt % to about 8.9 wt % TEA;

about 0.1 wt % to about 1.2 wt % triacetin;

about 0.9 wt % to about 2.9 wt % calcium stearate;

and about 58.6 wt % to about 60.6 wt % HA powder, preferably wherein the composition comprises:

about 0.9 wt % ALD;

about 28.6 wt % PCL;

about 0.9 wt % BDO;

about 7.9 wt % TEA;

about 0.2 wt % triacetin;

about 1.9 wt % calcium stearate; and about 59.6 wt % HA powder.

Embodiment 6. A composition comprising:

about 29.2 wt % to about 31.2 wt % ALD;

about 1.4 wt % to about 3.4 wt % PCL;

about 5.8 wt % to about 7.8 wt % tocopherol acetate;

about 55.2 wt % to about 57.2 wt % HA/β-TCP granules; and and about 3.4 wt % to about 5.4 wt % β-TCP powder, preferably wherein the composition comprises:

about 30.2 wt % ALD;

about 2.4 wt % PCL;

about 6.8 wt % tocopherol acetate;

about 56.2 wt % HA/β-TCP granules; and about 4.4 wt % β-TCP powder.

Embodiment 7. A composition comprising:

about 3.6 wt % to about 5.6 wt % ALD;

about 6.6 wt % to about 8.6 wt % PCL;

about 0.1 wt % to about 1.2 wt % BDO;

about 2.5 wt % to about 4.5 wt % tocopherol acetate;

about 2.1 wt % to about 4.1 wt % triacetin;

about 0.1 wt % to about 1.9 wt % calcium stearate;

about 13.6 wt % to about 15.6 wt % HA/β-TCP granules;

and about 64.4 wt % to about 66.4 wt % β-TCP powder, preferably wherein the composition comprises:

about 4.6 wt % ALD;

about 7.6 wt % PCL;

about 0.2 wt % BDO;

about 3.5 wt % tocopherol acetate;

about 3.1 wt % triacetin;

about 0.9 wt % calcium stearate;

about 14.6 wt % HA/β-TCP granules; and about 65.4 wt % β-TCP powder.

Embodiment 8. A composition comprising:

about 38.7 wt % to about 40.7 wt % ALD;

about 6.2 wt % to about 8.2 wt % tocopherol acetate;

about 0.01 wt % to about 1.1 wt % calcium stearate;

about 6.1 wt % to about 8.1 wt % β-TCP powder;

about 39.1 wt % to about 41.1 wt % HA powder;

and about 4.8 wt % to about 6.8 wt % barium sulfate, preferably wherein the composition comprises:

about 39.7 wt % ALD;

about 7.2 wt % tocopherol acetate;

about 0.1 wt % calcium stearate;

about 7.1 wt % β-TCP powder;

about 40.1 wt % HA powder; and about 5.8 wt % barium sulfate.

Embodiment 9. A composition comprising:

about 0.1 wt % to about 2 wt % ALD;

about 30.1 wt % to about 32.1 wt % PCL;

about 0.1 wt % to about 1.9 wt % BDO;

about 4.4 wt % to about 6.4 wt % TEA;

about 0.1 wt % to about 1.2 wt % triacetin;

about 0.9 wt % to about 2.9 wt % calcium stearate;

about 55.8 wt % to about 57.8.6 wt % HA powder; and about 1.8 wt % to about 3.8 wt % barium sulfate, preferably wherein the composition comprises:

about 1 wt % ALD;

about 31.1 wt % PCL;

about 0.9 wt % BDO;

about 5.4 wt % TEA;

about 0.2 wt % triacetin;

about 1.9 wt % calcium stearate;

about 56.8 wt % HA powder;

and about 2.8 wt % barium sulfate.

Embodiment 10. A composition comprising:

about 27.3 wt % to about 29.3 wt % TMPI;

about 2.3 wt % to about 4.3 wt % TMPE450;

about 1.9 wt % to about 3.9 wt % tocopherol acetate;

about 3.2 wt % to about 5.2 wt % parrafin oil;

about 28.2 wt % to about 30.2 wt % HA/β-TCP granules; and about 31.1 wt % to about 33.1 wt % β-TCP powder, preferably wherein the composition comprises:

about 28.3 wt % TMPI;

about 3.3 wt % TMPE450;

about 2.9 wt % tocopherol acetate;

about 4.2 wt % parrafin oil;

about 29.2 wt % HA/β-TCP granules; and about 32.1 wt % β-TCP powder.

Embodiment 11. A composition comprising:

about 2.9 wt % to about 4.9 wt % TMPI;

about 0.1 wt % to about 1.7 wt % TEA;

about 2.9 wt % to about 4.9 wt % TMPE170;

about 8.8 wt % to about 10.8 wt % TKP;

about 6.5 wt % to about 8.5 wt % tocopherol acetate;

about 2.7 wt % to about 4.7 wt % triacetin;

about 0.1 wt % to about 2 wt % parrafin oil; and about 68.5 wt % to about 70.5 wt % HA powder, preferably wherein the composition comprises:

about 3.9 wt % TMPI;

about 0.7 wt % TEA;

about 3.9 wt % TMPE170;

about 9.8 wt % TKP;

about 7.5 wt % tocopherol acetate;

about 3.7 wt % triacetin;

about 1 wt % parrafin oil;

and about 69.5 wt % HA powder.

Embodiment 12. A composition comprising:

about 5.8 wt % to about 7.8 wt % ALD;

about 4.2 wt % to about 6.2 wt % PCL;

about 0.9 wt % to about 2.9 wt % BDO;

about 2.7 wt % to about 4.7 wt % tocopherol acetate;

about 1.2 wt % to about 3.2 wt % triacetin;

about 0.1 wt % to about 1.5 wt % calcium stearate;

about 18 wt % to about 20 wt % HA/β-TCP granules;

about 58 wt % to about 60 wt % β-TCP powder; and about 0.7 wt % to about 2.7 wt % gentamicin, preferably wherein the composition comprises:

about 6.8 wt % ALD;

about 5.2 wt % PCL;

about 1.9 wt % BDO;

about 3.7 wt % tocopherol acetate;

about 2.2 wt % triacetin;

about 0.5 wt % calcium stearate;

about 19 wt % HA/β-TCP granules;

about 59 wt % β-TCP powder; and about 1.7 wt % gentamicin.

Embodiment 13. A composition comprising:
about 5.8 wt % to about 7.8 wt % ALD;
about 4.2 wt % to about 6.2 wt % PCL;
about 0.9 wt % to about 2.9 wt % BDO;
about 2.7 wt % to about 4.7 wt % tocopherol acetate;
about 1.2 wt % to about 3.2 wt % triacetin;
about 0.1 wt % to about 1.5 wt % calcium stearate;
about 18 wt % to about 20 wt % HA/β-TCP granules;
about 58 wt % to about 60 wt % β-TCP powder; and
about 0.7 wt % to about 2.7 wt % tobramycin,
preferably wherein the composition comprises:
    about 6.8 wt % ALD;
    about 5.2 wt % PCL;
    about 1.9 wt % BDO;
    about 3.7 wt % tocopherol acetate;
    about 2.2 wt % triacetin;
    about 0.5 wt % calcium stearate;
    about 19 wt % HA/β-TCP granules;
    about 59 wt % β-TCP powder; and
    about 1.7 wt % tobramycin.
Embodiment 14. A composition comprising:
about 4.3 wt % to about 6.3 wt % ALD;
about 4 wt % to about 6 wt % PCL;
about 0.8 wt % to about 2.8 wt % BDO;
about 2.6 wt % to about 4.6 wt % tocopherol acetate;
about 1.1 wt % to about 3.1 wt % triacetin;
about 0.1 wt % to about 1.5 wt % calcium stearate;
about 17.3 wt % to about 19.3 wt % HA/β-TCP granules;
about 55.9 wt % to about 57.9 wt % β-TCP powder;
and about 5.4 wt % to about 7.4 wt % vancomycin,
preferably wherein the composition comprises:
    about 5.3 wt % ALD;
    about 5 wt % PCL;
    about 1.8 wt % BDO;
    about 3.6 wt % tocopherol acetate;
    about 2.1 wt % triacetin;
    about 0.5 wt % calcium stearate;
    about 18.3 wt % HA/β-TCP granules;
    about 56.9 wt % β-TCP powder; and
    about 6.4 wt % vancomycin.
Embodiment 15. A composition comprising:
about 4.2 wt % to about 6.2 wt % ALD;
about 3.9 wt % to about 5.9 wt % PCL;
about 0.8 wt % to about 2.8 wt % BDO;
about 2.5 wt % to about 4.5 wt % tocopherol acetate;
about 1.1 wt % to about 3.1 wt % triacetin;
about 0.1 wt % to about 1.5 wt % calcium stearate;
about 17 wt % to about 19 wt % HA/β-TCP granules;
about 54.9 wt % to about 56.9 wt % β-TCP powder;
about 5.4 wt % to about 7.4 wt % vancomycin; and
about 0.7 wt % to about 2.7 wt % tobramycin or gentamycin,
preferably wherein the composition comprises:
    about 5.2 wt % ALD;
    about 4.9 wt % PCL;
    about 1.8 wt % BDO;
    about 3.5 wt % tocopherol acetate;
    about 2.1 wt % triacetin;
    about 0.5 wt % calcium stearate;
    about 18 wt % HA/β-TCP granules;
    about 55.9 wt % β-TCP powder;
    about 6.4 wt % vancomycin;
    and about 1.7 wt % tobramycin or gentamycin.
Embodiment 16. A kit comprising at least one amount of a first composition and at least one amount of a second composition, wherein:

i) the first composition is the composition of Embodiment 1 and the second composition is the composition of Embodiment 2;
  ii) the first composition is the composition of Embodiment 1 and the second composition is the composition of Embodiment 3;
  iii) the first composition is the composition of Embodiment 4 and the second composition is the composition of Embodiment 5;
  iv) the first composition is the composition of Embodiment 6 and the second composition is the composition of Embodiment 7;
  v) the first composition is the composition of Embodiment 8 and the second composition is the composition of Embodiment 9;
  vi) the first composition is the composition of Embodiment 10 and the second composition is the composition of Embodiment 11;
  vii) the first composition is the composition of Embodiment 1 and the second composition is the composition of Embodiment 12;
  viii) the first composition is the composition of Embodiment 1 and the second composition is the composition of Embodiment 13;
  ix) the first composition is the composition of Embodiment 1 and the second composition is the composition of Embodiment 14; or
  x) the first composition is the composition of Embodiment 1 and the second composition is the composition of Embodiment 15.
Embodiment 17. A settable composition formed by mixing a first composition and a second composition, wherein
  i) the first composition is the composition of Embodiment 1 and the second composition is the composition of Embodiment 2;
  ii) the first composition is the composition of Embodiment 1 and the second composition is the composition of Embodiment 3;
  iii) the first composition is the composition of Embodiment 4 and the second composition is the composition of Embodiment 5;
  iv) the first composition is the composition of Embodiment 6 and the second composition is the composition of Embodiment 7;
  v) the first composition is the composition of Embodiment 8 and the second composition is the composition of Embodiment 9;
  vi) the first composition is the composition of Embodiment 10 and the second composition is the composition of Embodiment 11;
  vii) the first composition is the composition of Embodiment 1 and the second composition is the composition of Embodiment 12;
  viii) the first composition is the composition of Embodiment 1 and the second composition is the composition of Embodiment 13;
  ix) the first composition is the composition of Embodiment 1 and the second composition is the composition of Embodiment 14; or
  x) the first composition is the composition of Embodiment 1 and the second composition is the composition of Embodiment 15.
Embodiment 18. A method of stabilizing a bone fracture or reapproximating a sternotomy, the method comprising:
  a) mixing together a first composition and a second composition, wherein i) the first composition is the composition of Embodiment 1 and the second composition is the composition of Embodiment 2;

ii) the first composition is the composition of Embodiment 1 and the second composition is the composition of Embodiment 3;

iii) the first composition is the composition of Embodiment 4 and the second composition is the composition of Embodiment 5;

iv) the first composition is the composition of Embodiment 6 and the second composition is the composition of Embodiment 7;

v) the first composition is the composition of Embodiment 8 and the second composition is the composition of Embodiment 9;

vi) the first composition is the composition of Embodiment 10 and the second composition is the composition of Embodiment 11;

vii) the first composition is the composition of Embodiment 1 and the second composition is the composition of Embodiment 12;

viii) the first composition is the composition of Embodiment 1 and the second composition is the composition of Embodiment 13;

ix) the first composition is the composition of Embodiment 1 and the second composition is the composition of Embodiment 14; or x) the first composition is the composition of Embodiment 1 and the second composition is the composition of Embodiment 15;

b) applying the mixed composition to the surfaces of the bone fracture or the cut surfaces of the sternotomy; and c) reducing the bone fracture or reapproximating the sternum while allowing the mixed composition to set.

Embodiment 19. The method of Embodiment 18, wherein step (b) further comprises:

i) applying a portion of the mixed composition across the surface of at least one surgical hardware to create a mixed composition-hardware construct; and ii) affixing the mixing composition-hardware construct to the surfaces of the bone fracture or the cut surfaces of the sternotomy.

Embodiment 20. The method of Embodiment 18, wherein the surgical hardware is any one of a plate, a screw, a mesh, a nail, a cap, a wire, a flap or a combination thereof.

Embodiment 21. The method of any one of Embodiment 18-20, wherein the bone fracture is any one of a cranial bone fracture or defect, a pelvic bone fracture or defect or long bone fracture.

Embodiment 22. A method of treating brain cancer, the method comprising:

a) implanting a radiation therapy device in a subject via a cranial flap;

b) mixing together a first composition and a second composition, wherein i) the first composition is the composition of Embodiment 1 and the second composition is the composition of Embodiment 2;

ii) the first composition is the composition of Embodiment 1 and the second composition is the composition of Embodiment 3;

iii) the first composition is the composition of Embodiment 4 and the second composition is the composition of Embodiment 5;

iv) the first composition is the composition of Embodiment 6 and the second composition is the composition of Embodiment 7;

v) the first composition is the composition of Embodiment 8 and the second composition is the composition of Embodiment 9;

vi) the first composition is the composition of Embodiment 10 and the second composition is the composition of Embodiment 11;

vii) the first composition is the composition of Embodiment 1 and the second composition is the composition of Embodiment 12;

viii) the first composition is the composition of Embodiment 1 and the second composition is the composition of Embodiment 13;

ix) the first composition is the composition of Embodiment 1 and the second composition is the composition of Embodiment 14; or x) the first composition is the composition of Embodiment 1 and the second composition is the composition of Embodiment 15; and c) sealing the cranial flap using the final product composition.

Embodiment 23. A composition comprising about 19.5 wt % to about 21.5 wt % ALD;

about 3 wt % to about 5 wt % PCL;

about 0.1 wt % to about 2 wt % BDO;

about 4.2 wt % to about 6.2 wt % tocopherol acetate;

about 0.1 wt % to about 2.1 wt % triacetin;

about 0.1 wt % to about 1.3 wt % calcium stearate;

about 34.5 wt % to about 36.5 wt % HA/β-TCP granules; and about 31.5 wt % to about 33.5 wt % β-TCP powder;

preferably wherein the composition comprises about 20.5 wt % ALD;

about 4 wt % PCL;

about 1 wt % BDO;

about 5.2 wt % tocopherol acetate;

about 1.1 wt % triacetin;

about 0.3 wt % calcium stearate;

about 35.5 wt % HA/β-TCP granules; and about 32.5 wt % β-TCP powder.

Embodiment 24. A composition comprising:

about 20.1 wt % to about 22.1 wt % ALD;

about 2.3 wt % to about 5.3 wt % PCL;

about 0.1 wt % to about 1.5 wt % BDO;

about 0.2 wt % to about 2.2 wt % TEA;

about 4.6 wt % to about 6.6 wt % tocopherol acetate;

about 0.1 wt % to about 2 wt % triacetin;

about 0.1 wt % to about 1.2 wt % calcium stearate;

about 34.3 wt % to about 36.3 wt % HA/β-TCP granules; and and about 30.8 wt % to about 32.8 wt % β-TCP powder;

preferably wherein the composition comprises:

about 21.1 wt % ALD;

about 3.3 wt % PCL;

about 0.5 wt % BDO;

about 1.2 wt % TEA;

about 5.6 wt % tocopherol acetate;

about 1 wt % triacetin;

about 0.2 wt % calcium stearate;

about 35.3 wt % HA/β-TCP granules;

and about 31.8 wt % β-TCP powder.

Embodiment 25. A composition comprising:

about 31.3 wt % to about 33.3 wt % ALD;

about 4.6 wt % to about 6.6 wt % PCL;

about 0.1 wt % to about 1.2 wt % BDO;

about 0.6 wt % to about 2.6 wt % TEA;

about 4.8 wt % to about 6.8 wt % tocopherol acetate;

about 0.1 wt % to about 1.4 wt % calcium stearate;

about 5.4 wt % to about 7.4 wt % β-TCP powder;
and about 46.8 wt % to about 48.8 wt % HA powder;
preferably wherein the composition comprises:
  about 32.3 wt % ALD;
  about 5.6 wt % PCL;
  about 0.2 wt % BDO;
  about 1.6 wt % TEA;
  about 5.8 wt % tocopherol acetate;
  about 0.4 wt % calcium stearate;
  about 6.4 wt % β-TCP powder; and
  about 47.8 wt % HA powder.
Embodiment 26. A composition comprising:
about 16.4 wt % to about 18.4 wt % ALD;
about 4 wt % to about 6 wt % PCL;
about 0.01 wt % to about 1.1 wt % BDO;
about 4.1 wt % to about 6.1 wt % tocopherol acetate;
about 0.5 wt % to about 2.5 wt % triacetin;
about 0.1 wt % to about 1.5 wt % calcium stearate;
about 34.4 wt % to about 36.4 wt % HA/β-TCP granules;
  and
about 33.9 wt % to about 35.9 wt % β-TCP powder;
preferably wherein the composition comprises:
  about 17.4 wt % ALD;
  about 5 wt % PCL;
  about 0.1 wt % BDO;
  about 5.1 wt % tocopherol acetate;
  about 1.5 wt % triacetin;
  about 0.5 wt % calcium stearate;
  about 35.4 wt % HA/β-TCP granules; and
  about 34.9 wt % β-TCP powder.
Embodiment 27. A composition comprising:
about 31.1 wt % to about 33.1 wt % ALD;
about 5.1 wt % to about 7.1 wt % PCL;
about 0.1 wt % to about 1.2 wt % BDO;
about 0.1 wt % to about 2.1 wt % TEA;
about 4.8 wt % to about 6.8 wt % tocopherol acetate;
about 0.1 wt % to about 1.4 wt % calcium stearate;
about 4.7 wt % to about 6.7 wt % β-TCP powder;
about 42.4 wt % to about 44.4 wt % HA powder; and
about 4.2 wt % to about 6.2 wt % barium sulfate;
preferably wherein the composition comprises:
  about 32.1 wt % ALD;
  about 6.1 wt % PCL;
  about 0.2 wt % BDO;
  about 1.1 wt % TEA;
  about 5.8 wt % tocopherol acetate;
  about 0.4 wt % calcium stearate;
  about 5.7 wt % β-TCP powder;
  about 43.4 wt % HA powder;
  and about 5.2 wt % barium sulfate.
Embodiment 28. A composition comprising:
about 16.9 wt % to about 18.9 wt % TMPI;
about 0.1 wt % to about 1.3 wt % TEA;
about 0.7 wt % to about 2.7 wt % TMPE170;
about 0.9 wt % to about 2.9 wt % TMPE450;
about 3.2 wt % to about 5.2 wt % TKP;
about 3.8 wt % to about 5.8 wt % tocopherol acetate;
about 0.6 wt % to about 2.6 wt % triacetin;
about 1.9 wt % to about 3.9 wt % paraffin oil;
about 15.7 wt % to about 17.7 wt % HA/β-TCP granules;
about 17.4 wt % to about 19.4 wt % β-TCP powder; and
about 28.8 wt % to about 30.8 wt % HA powder;
preferably wherein the composition comprises:
  about 17.9 wt % TMPI;
  about 0.3 wt % TEA;
  about 1.7 wt % TMPE170;
  about 1.9 wt % TMPE450;

about 4.2 wt % TKP;
  about 4.8 wt % tocopherol acetate;
  about 1.6 wt % triacetin;
  about 2.9 wt % paraffin oil;
  about 16.7 wt % HA/β-TCP granules;
  about 18.4 wt % β-TCP powder; and
  about 29.8 wt % HA powder.
Embodiment 29. A composition comprising:
about 19.4 wt % to about 21.4 wt % ALD;
about 3 wt % to about 5 wt % PCL;
about 0.1 wt % to about 1.9 wt % BDO;
about 4.1 wt % to about 6.1 wt % tocopherol acetate;
about 0.1 wt % to about 2.1 wt % triacetin;
about 0.1 wt % to about 1.3 wt % calcium stearate;
about 34.4 wt % to about 36.4 wt % HA/β-TCP granules;
about 31 wt % to about 33 wt % β-TCP powder; and
about 0.1 wt % to about 1.8 wt % gentamicin;
preferably wherein the composition comprises:
  about 20.4 wt % ALD;
  about 4 wt % PCL;
  about 0.9 wt % BDO;
  about 5.1 wt % tocopherol acetate;
  about 1.1 wt % triacetin;
  about 0.3 wt % calcium stearate;
  about 35.4 wt % HA/β-TCP granules;
  about 32 wt % β-TCP powder; and
  about 0.8 wt % gentamicin.
Embodiment 30. A composition comprising:
about 19.4 wt % to about 21.4 wt % ALD;
about 3 wt % to about 5 wt % PCL;
about 0.1 wt % to about 1.9 wt % BDO;
about 4.1 wt % to about 6.1 wt % tocopherol acetate;
about 0.1 wt % to about 2.1 wt % triacetin;
about 0.1 wt % to about 1.3 wt % calcium stearate;
about 34.4 wt % to about 36.4 wt % HA/β-TCP granules;
about 31 wt % to about 33 wt % β-TCP powder;
and about 0.1 wt % to about 1.8 wt % tobramycin;
preferably wherein the composition comprises:
  about 20.4 wt % ALD;
  about 4 wt % PCL;
  about 0.9 wt % BDO;
  about 5.1 wt % tocopherol acetate;
  about 1.1 wt % triacetin;
  about 0.3 wt % calcium stearate;
  about 35.4 wt % HA/β-TCP granules;
  about 32 wt % β-TCP powder; and
  about 0.8 wt % tobramycin.
Embodiment 31. A composition comprising:
about 18.7 wt % to about 20.7 wt % ALD;
about 2.9 wt % to about 4.9 wt % PCL;
about 0.1 wt % to about 1.9 wt % BDO;
about 4.1 wt % to about 6.1 wt % tocopherol acetate;
about 0.1 wt % to about 2.1 wt % triacetin;
about 0.1 wt % to about 1.3 wt % calcium stearate;
about 34 wt % to about 36 wt % HA/β-TCP granules;
about 29.9 wt % to about 31.9 wt % β-TCP powder; and
about 2.2 wt % to about 4.2 wt % vancomycin;
preferably wherein the composition comprises:
  about 19.7 wt % ALD;
  about 3.9 wt % PCL;
  about 0.9 wt % BDO;
  about 5.1 wt % tocopherol acetate;
  about 1.1 wt % triacetin;
  about 0.3 wt % calcium stearate;
  about 35 wt % HA/β-TCP granules;
  about 30.9 wt % β-TCP powder; and
  about 3.2 wt % vancomycin.

Embodiment 32. A composition comprising:
about 18.7 wt % to about 20.7 wt % ALD;
about 2.8 wt % to about 4.8 wt % PCL;
about 0.1 wt % to about 1.9 wt % BDO;
about 4 wt % to about 6 wt % tocopherol acetate;
about 0.1 wt % to about 2.1 wt % triacetin;
about 0.1 wt % to about 1.3 wt % calcium stearate;
about 33.9 wt % to about 35.9 wt % HA/β-TCP granules;
about 29.4 wt % to about 31.4 wt % β-TCP powder;
about 2.2 wt % to about 4.2 wt % vancomycin; and
about 0.1% to about 1.8% tobramycin or gentamycin;
preferably wherein the composition comprises:
about 19.7 wt % ALD;
about 3.8 wt % PCL;
about 0.9 wt % BDO;
about 5 wt % tocopherol acetate;
about 1.1 wt % triacetin;
about 0.3 wt % calcium stearate;
about 34.9 wt % HA/β-TCP granules;
about 30.4 wt % β-TCP powder;
about 3.2 wt % vancomycin; and
about 0.8% tobramycin or gentamycin.

Embodiment 33. A method of stabilizing a bone fracture or reapproximating a sternotomy, the method comprising:
a) applying the composition of any one of Embodiments 23-32 to the surfaces of the bone fracture or the cut surfaces of the sternotomy; and
b) reducing the bone fracture or reapproximating the sternum while allowing the mixed composition to set.

Embodiment 34. The method of Embodiment 18, wherein step (a) further comprises:
i) applying a portion of the composition across the surface of at least one surgical hardware to create a composition-hardware construct; and
ii) affixing the composition-hardware construct to the surfaces of the bone fracture or the cut surfaces of the sternotomy.

Embodiment 35. The method of Embodiment 34, wherein the surgical hardware is any one of a plate, a screw, a mesh, a nail, a cap, a wire, a flap or a combination thereof.

Embodiment 36. The method of any one of Embodiments 33-35, wherein the bone fracture is any one of a cranial bone fracture or defect, a pelvic bone fracture or defect or long bone fracture.

Embodiment 37. A method of treating brain cancer, the method comprising:
a) implanting a radiation therapy device in a subject via a cranial flap;
b) sealing the cranial flap using the composition of any one of Embodiments 23-32.

EQUIVALENTS

The details of one or more aspects and/or embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms may include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

What is claimed is:

1. A first reactive composition and a second reactive composition, the first reactive composition comprising:
about 38.9 wt % to about 40.9 wt % ALD;
about 6.2 wt % to about 8.2 wt % tocopherol acetate;
about 0.01 wt % to about 1.1 wt % calcium stearate;
about 6.9 wt % to about 8.9 wt % β-TCP powder; and
about 43.8 wt % to about 45.8 wt % HA powder; and
the second reactive composition comprising:
about 0.1 wt % to about 1.9 wt % ALD;
about 27.6 wt % to about 29.6 wt % PCL;
about 0.1 wt % to about 1.9 wt % BDO;
about 6.9 wt % to about 8.9 wt % TEA;
about 0.1 wt % to about 1.2 wt % triacetin;
about 0.9 wt % to about 2.9 wt % calcium stearate;
and about 58.6 wt % to about 60.6 wt % HA powder.

2. A kit comprising the first reactive composition and the second reactive composition of claim 1.

3. A settable composition formed by mixing the first composition and the second composition of claim 1.

4. A method of stabilizing a bone fracture or reapproximating a sternotomy, the method comprising:
a) mixing together the first reactive composition and the second reactive composition of claim 1 to form a settable composition;
b) applying the settable composition to the surfaces of the bone fracture or the cut surfaces of the sternotomy; and
c) reducing the bone fracture or reapproximating the sternum while allowing the settable composition to set.

5. The method of claim 4, wherein step (b) further comprises:
i) applying a portion of the settable composition across the surface of at least one surgical hardware to create a mixed composition-hardware construct; and
ii) affixing the mixing composition-hardware construct to the surfaces of the bone fracture or the cut surfaces of the sternotomy.

6. The method of claim 5, wherein the surgical hardware is any one of a plate, a screw, a mesh, a nail, a cap, a wire, a flap or a combination thereof.

7. The method of claim 4, wherein the bone fracture is any one of a cranial bone fracture or defect, a pelvic bone fracture or defect or long bone fracture.

8. A settable composition of claim 4, wherein the settable composition comprises:
about 31.3 wt % to about 33.3 wt % ALD;
about 4.6 wt % to about 6.6 wt % PCL;
about 0.1 wt % to about 1.2 wt % BDO;
about 0.6 wt % to about 2.6 wt % TEA;
about 4.8 wt % to about 6.8 wt % tocopherol acetate;
about 0.1 wt % to about 1.4 wt % calcium stearate;
about 5.4 wt % to about 7.4 wt % β-TCP powder;
and about 46.8 wt % to about 48.8 wt % HA powder.

9. A method of stabilizing a bone fracture or reapproximating a sternotomy, the method comprising:
a) applying the settable composition of claim 8 to the surfaces of the bone fracture or the cut surfaces of the sternotomy; and
b) reducing the bone fracture or reapproximating the sternum while allowing the settable composition to set.

10. The method of claim 9, wherein step (a) further comprises:

i) applying a portion of the settable composition across the surface of at least one surgical hardware to create a composition-hardware construct; and ii) affixing the composition-hardware construct to the surfaces of the bone fracture or the cut surfaces of the sternotomy.

11. The method of claim 10, wherein the surgical hardware is any one of a plate, a screw, a mesh, a nail, a cap, a wire, a flap, or a combination thereof.

12. The method of claim 9, wherein the bone fracture is any one of a cranial bone fracture or defect, a pelvic bone fracture or defect, or a long bone fracture.

13. A method of treating brain cancer, the method comprising:

a) implanting a radiation therapy device in a subject via a cranial flap; and b) sealing the cranial flap using the settable composition of claim 8.

14. The settable composition of claim 8, wherein the settable composition comprises:

about 32.3 wt % ALD;

about 5.6 wt % PCL;

about 0.2 wt % BDO;

about 1.6 wt % TEA;

about 5.8 wt % tocopherol acetate;

about 0.4 wt % calcium stearate;

about 6.4 wt % β-TCP powder; and about 47.8 wt % HA powder.

15. A method of treating brain cancer, the method comprising:

a) implanting a radiation therapy device in a subject via a cranial flap;

b) mixing together the first reactive composition and the second reactive composition of claim 1 to form a settable composition;

c) sealing the cranial flap using the settable composition.

16. The first reactive composition and second reactive composition of claim 1, wherein the first reactive composition comprises:

about 39.9 wt % ALD;

about 7.2 wt % tocopherol acetate;

about 0.1 wt % calcium stearate;

about 7.9 wt % β-TCP powder; and about 44.8 wt % HA powder; and the second reactive composition comprises:

about 0.9 wt % ALD;

about 28.6 wt % PCL;

about 0.9 wt % BDO;

about 7.9 wt % TEA;

about 0.2 wt % triacetin;

about 1.9 wt % calcium stearate; and about 59.6 wt % HA powder.

\* \* \* \* \*